(12) United States Patent
Stone et al.

(10) Patent No.: US 11,419,494 B1
(45) Date of Patent: **\*Aug. 23, 2022**

(54) FIELD-DEPLOYABLE NEUROLOGICAL ASSESSMENT TOOL FOR PERFORMANCE READINESS AND TELEMEDICINE

(71) Applicant: United States of America as Represented by the Administrator of NASA, Washington, DC (US)

(72) Inventors: Leland Scott Stone, San Francisco, CA (US); Dorion Bryce Liston, Boulder Creek, CA (US); Bernard Dov Adelstein, San Mateo, CA (US); Mark Richard Anderson, San Carlos, CA (US); Kenji Hiroshi Kato, San Jose, CA (US)

(73) Assignee: United States of America as Represented by the Administrator of NASA, Washington, DC (US)

( * ) Notice: Subject to any disclaimer, the term of this patent is extended or adjusted under 35 U.S.C. 154(b) by 71 days.

This patent is subject to a terminal disclaimer.

(21) Appl. No.: 16/579,824

(22) Filed: Sep. 23, 2019

Related U.S. Application Data

(60) Continuation-in-part of application No. 15/676,875, filed on Aug. 14, 2017, now Pat. No. 10,463,249, which is a division of application No. 14/710,260, filed on May 12, 2015, now Pat. No. 9,730,582, and application No. 16/579,824, Sep. 23, 2019, which is
(Continued)

(51) Int. Cl.
*A61B 3/113* (2006.01)
*A61B 3/00* (2006.01)
*A61B 3/032* (2006.01)
*A61B 3/024* (2006.01)

(52) U.S. Cl.
CPC ............ *A61B 3/113* (2013.01); *A61B 3/0025* (2013.01); *A61B 3/0041* (2013.01); *A61B 3/0091* (2013.01); *A61B 3/024* (2013.01); *A61B 3/032* (2013.01)

(58) Field of Classification Search
CPC ..... A61B 3/113; A61B 3/0041; A61B 3/0091; A61B 3/032; A61B 3/0025; A61B 3/10
USPC ................... 351/209, 210; 382/103; 600/558
See application file for complete search history.

(56) References Cited

U.S. PATENT DOCUMENTS 4,889,422 A \* 12/1989 Pavlidis ................. G16H 15/00
351/210
10,420,465 B1 \* 9/2019 Stone ..................... A61B 3/032
(Continued)

OTHER PUBLICATIONS

"Oculometric Assessment of Dynamic Visual Processing", Journal of Vision, 2014.\*

*Primary Examiner* — Jordan M Schwartz
(74) *Attorney, Agent, or Firm* — Rhys W. Cheung; Robert M. Padilla; Helen M. Gaius

(57) ABSTRACT

Provided is a portable, hand-held, self-powered, self-calibrated, easy-to-use "iCOBRA" system, a neural/neurological assessment tool for both operational decision-making in military, aerospace, sports, and other high-performance settings, and to assist in diagnostics in medical practice. The system harnesses multimodal 3D imaging technologies for robust, calibration free, head and eye tracking to allow for visual, vestibular, and oculomotor assessment of human neural health and performance.

15 Claims, 10 Drawing Sheets

Related U.S. Application Data a continuation-in-part of application No. 15/707,561, filed on Sep. 18, 2017, now Pat. No. 10,420,465.

(60) Provisional application No. 61/994,673, filed on May 16, 2014, provisional application No. 62/395,927, filed on Sep. 16, 2016, provisional application No. 62/823,648, filed on Mar. 25, 2019.

(56) References Cited

U.S. PATENT DOCUMENTS

| | | | | |
|---|---|---|---|---|
| 2014/0313488 A1* | 10/2014 | Kiderman | .............. | A61B 3/113 351/246 |
| 2017/0135577 A1* | 5/2017 | Komogortsev | ...... | A61B 5/7282 |

* cited by examiner

FIG. 1A
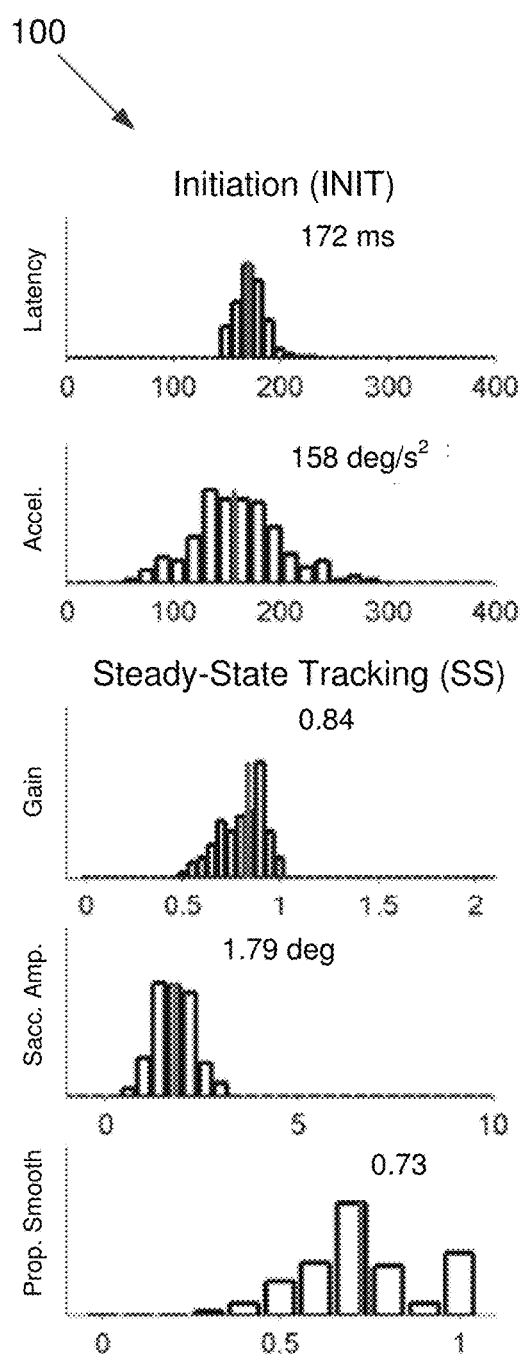
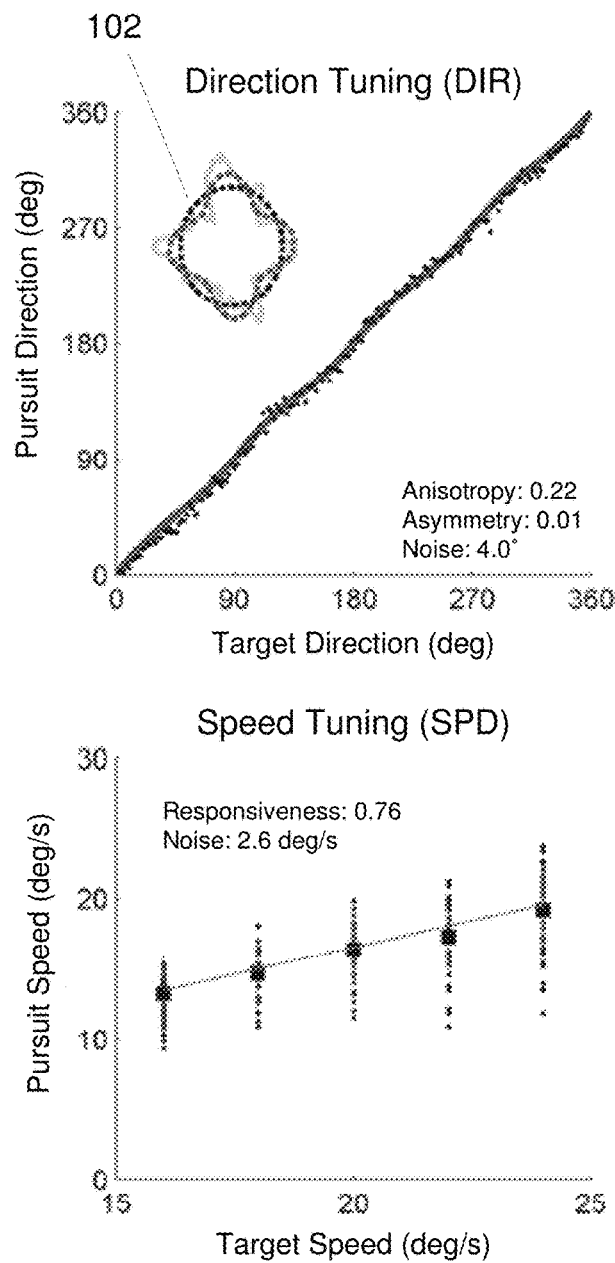

FIG. 1B
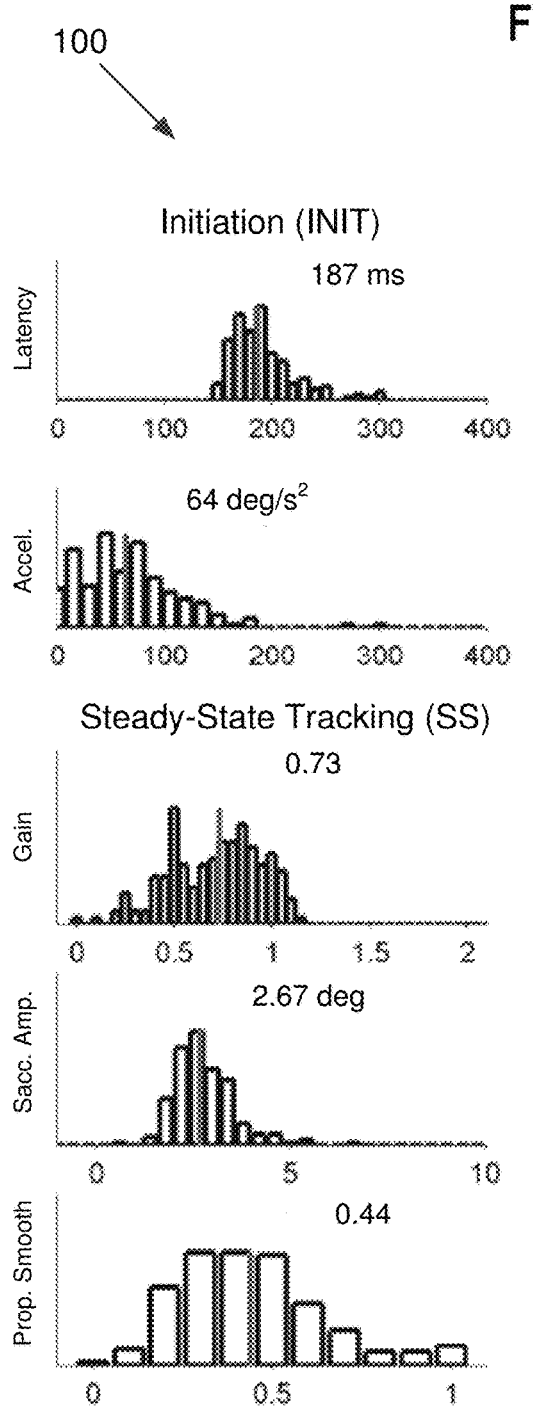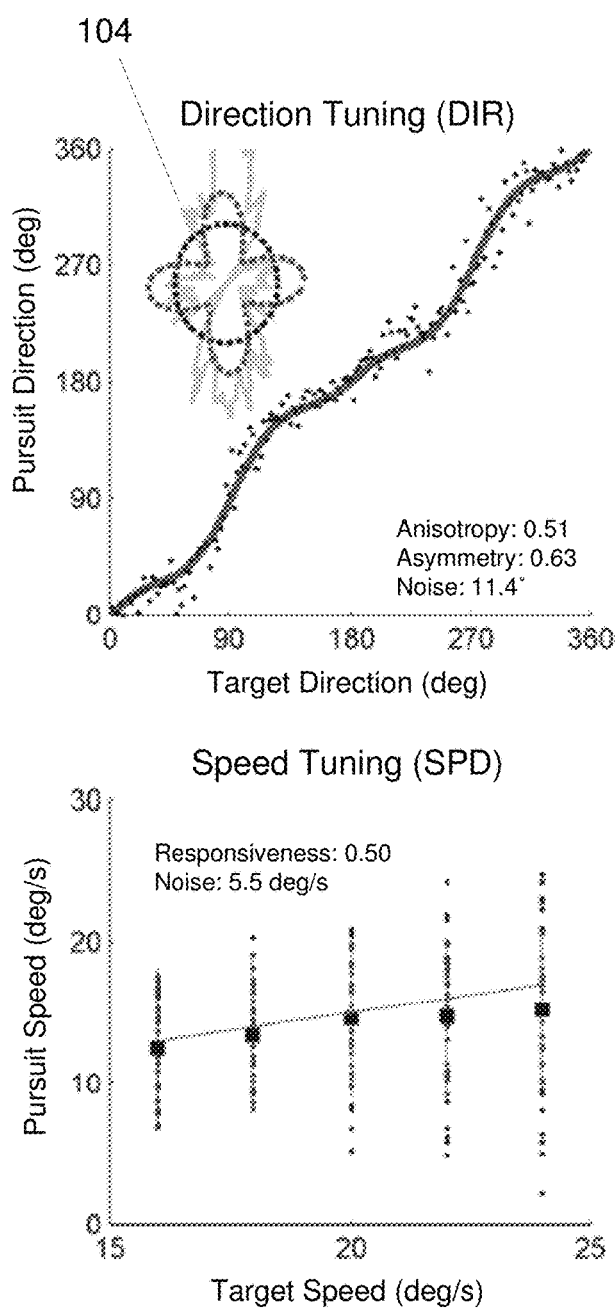

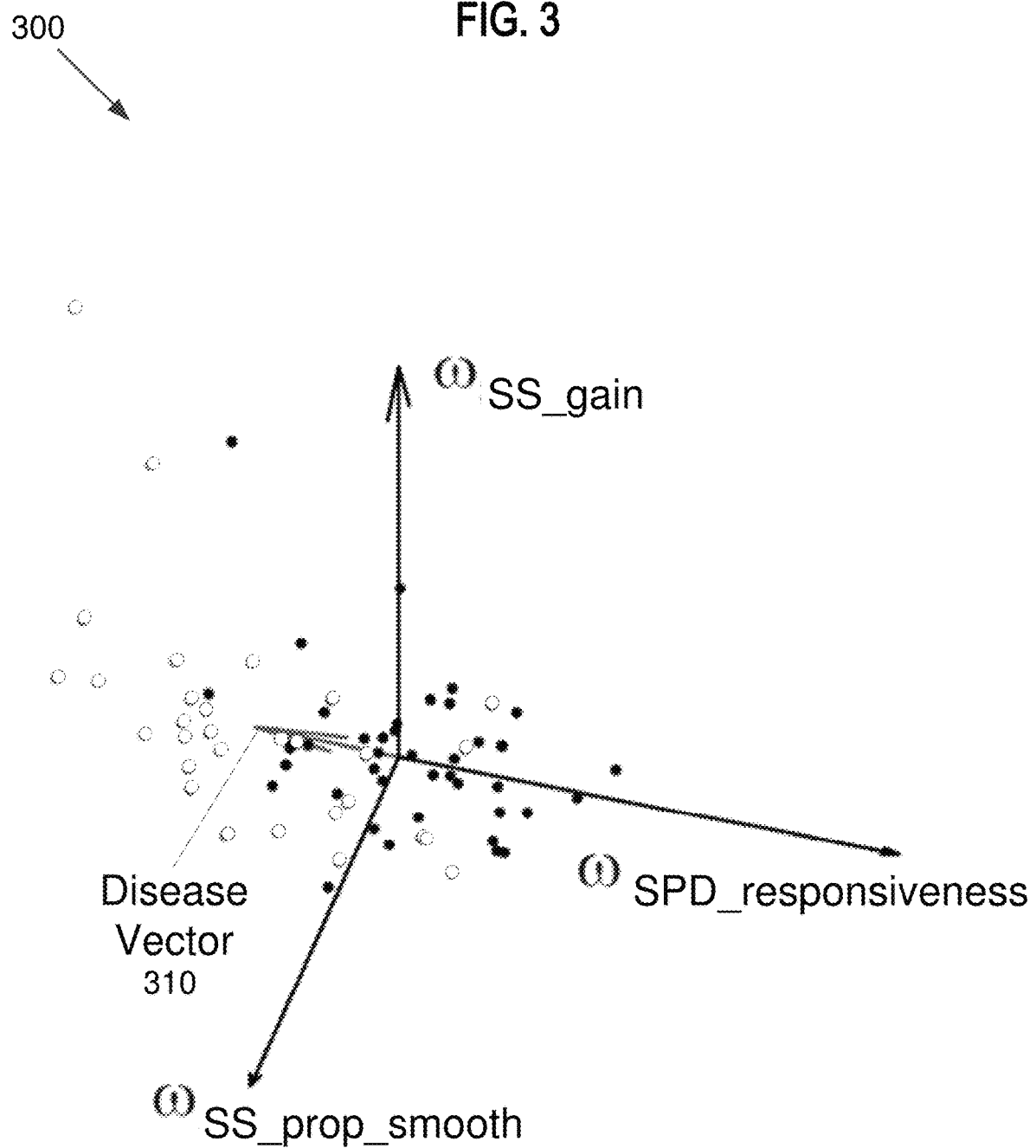

FIELD-DEPLOYABLE NEUROLOGICAL ASSESSMENT TOOL FOR PERFORMANCE READINESS AND TELEMEDICINE

CROSS-REFERENCE TO RELATED APPLICATION

This application is a continuation-in-part of U.S. patent application Ser. No. 15/707,561 filed Sep. 18, 2017, which claims the benefit of U.S. Provisional Patent Application No. 62/395,927 filed Sep. 16, 2016, and is a continuation-in-part of U.S. patent application Ser. No. 15/676,875 filed Aug. 14, 2017, which is a divisional of U.S. patent application Ser. No. 14/710,260 filed May 12, 2015, now issued as U.S. Pat. No. 9,730,582, which claims the benefit of U.S. Provisional Patent Application No. 61/994,673 filed May 16, 2014. This application also claims the benefit of U.S. Provisional Patent Application No. 62/823,648, filed Mar. 25, 2019. The subject matter of these earlier filed applications is hereby incorporated by reference in its entirety.

ORIGIN OF THE INVENTION

The invention described herein was made in the performance of work under a NASA contract by employees of the Arctic Slope Regional Corporation Research & Technology Solutions and by employees of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor elected not to retain title.

FIELD

The present invention generally relates to neuro-functional assessment, and more particularly, to field-deployable neurological assessment tools.

BACKGROUND

Diffuse tissue damage from impact or blast traumatic brain injury (TBI), various illnesses, intoxication due to drugs or alcohol, sleep deprivation, and the like degrade information processing by the brain, often resulting in impairments in sensorimotor function. Deficits in dynamic visual processing, smooth-pursuit tracking, saccadic eye movements, the pupillary light reflex, or vestibulo-ocular reflexes can indicate that such an impairment exists. Indeed, eye movements are the most frequent, biomechanically-simplest, voluntary, visually-driven motor responses, providing a model system to assess the sequelae of brain insult, injury, and impairment. For more than a century, neurologists, psychologists, and psychiatrists have recognized that oculomotor behavior can reflect functional consequences of neural pathology, resulting in an extensive catalogue of qualitative oculomotor signs of drug toxicity, brain injury, and neurological disease, as well as standard ranges for normal behavior on common tasks.

Thus, oculomotor exams are used in both clinical (e.g., localizing lesions, diagnosing vestibular disorders, and detecting cranial nerve palsies) and field (e.g., detecting alcohol intoxication and fatigue) settings. Following TBI, oculomotor signs, such as disconjugate gaze, impaired saccadic inhibition, increased movement latency, amplified directional error, and impaired predictive tracking, have been reported, all consistent with impaired visual processing with ataxia and sway and other indicators of impaired vestibular processing (both otolith and canal function) as well. However, the need for a readily-available clinical tool to quantitatively and systematically assess visual motion processing and vestibular function persists. To this end, leaders in the oculomotor field have proposed using oculomotor metrics as biomarkers of disease or trauma associated with both visual and vestibular dysfunction within cortical (e.g. examining direction and speed processing), cerebellar (e.g., examining fixational stability), and brainstem (e.g. examining saccadic velocity and saccadic dynamics) pathways.

Certain oculometric approaches employ large and heavy, cumbersome, high power consumption instruments that require some expertise to run and are sensitive to head-movement artifacts that could become even more problematic for use in an operational setting. These devices require repeated calibration, and are impractical for field deployment.

It is desirable to have a performance-based technology that does not require such calibration.

SUMMARY

Certain embodiments of the present invention may provide solutions to the problems and needs in the art that have not yet been fully identified, appreciated, or solved by conventional clinical neuro-functional processing assessment technologies. For example, some embodiments of the present invention improves the capability of the original Comprehensive Oculomotor Behavioral Response Assessment (COBRA) system by harnessing multimodal 3D imaging technologies for robust, calibration free, head and eye tracking to allow for visual, vestibular, and oculomotor assessment of human neural health and performance.

Some embodiments of the invention measure head movement assess vestibular function (both otolith and canal function). These embodiments distinguish visual and vestibular eye movements in the head from those in the world trivially caused by head movement.

Some embodiments of the invention provide the advantages of being a small, lightweight, low-power, easy-to-use system that does not require repeated calibration, and could be instantiated as a hand-held device that is immune to head-movement artifacts, does not require a stabilized display, and thus appropriate for operational deployment. Other objectives is to extend current visual and visuomotor testing to include an assessment of vestibular function that can distinguish between otolith and canal driven responses.

According to some embodiments, the system is configured to diagnose a condition by deriving a sensitive indicator of the likelihood of a particular disease or injury state based on results of an eye-movement assessment test that includes an appropriately randomized, radial visual tracking task and auditory-paced (to set the stimulus frequency), stereotyped head movements at different viewing distances and different frequencies, together with a broad set of oculometric measures to assess and distinguish neural function in visual, otolith and canal driven neural pathways and their frequency responses (because otolith responses will be viewing distance-dependent and canal responses will not). The set of oculometric measures may be combined into a single scalar to yield the sensitive overall indicator of sensorimotor functional status. More specifically, for any given clinical condition, an "impairment vector" may be defined by the direction of the deviation in the multi-dimensional space of oculomotor measures between the mean of the relevant specific patient population and the mean of the normal population. The inner product between such a specific impairment vector and the multi-dimensional oculomotor performance vector of any individual yields a linear detection metric of the severity of their impairment (i.e., their "impairment index") along the tested impairment vector with specificity potentially further enhanced through the absence or paucity of impairment along other tested "impairment vector" directions.

In some embodiments, the impairment vector for TBI (or alcohol, or fatigue or *cannabis*, or CO2 level etc.) could be used to measure an individual's likelihood of having suffered from a TBI (or be adversely affected by alcohol, or fatigue, or *cannabis*, or CO2 level etc.) by showing that the TBI (alcohol, fatigue, *cannabis*, or CO2 etc.) index (a specific impairment index, see below) is significantly elevated compared to that of the normal population (or with respect to a baseline measure from the same individual). Further specificity in such a suggested diagnosis could be achieved by measuring other impairment indices associated with other impairment vectors. For example, an alcohol intoxication index or a fatigue index could be computed using the alcohol and fatigue vectors, respectively, to determine the relative likelihood that observed symptoms or deficits might be caused by factors other than TBI, such as alcohol or fatigue or *cannabis*, or CO2 level etc.

In an embodiment, a computer-implemented method includes creating search templates for a plurality of conditions, by a computing system, and performing oculometric testing on an individual, by the computing system. The computer-implemented method also includes creating a vector for the individual, by the computing system, based on the oculometric testing, and analyzing the vector for the individual, by the computing system, against one or more of the search templates to produce an impairment index that maps the vector for the individual to the one or more search templates. The computer-implemented method further includes outputting results of the analysis for review, by the computing system.

In another embodiment, a computer program is embodied on a non-transitory computer-readable medium. The program is configured to cause at least one processor to perform oculometric testing on an individual and create a vector for the individual based on the oculometric testing. The computer program is also configured to cause the at least one processor to analyze the vector for the individual against a search template to produce an impairment index that maps the vector for the individual to the search template and output results of the analysis for review.

In yet another embodiment, a computing system includes memory storing computer program code for performing oculometric assessment of sensorimotor impairment and at least one processor configured to execute the computer program code. The computing system is configured to perform oculometric testing on an individual and create a vector for the individual based on the oculometric testing. The computing system is also configured to analyze the vector for the individual against a search template and produce an impairment index based on the analysis that maps the vector for the individual to the search template.

In a further embodiment, a computer-implemented method includes displaying a tracking target, by a computing system, at an initial location on a display for a randomized delay interval. After the randomized delay interval has elapsed, the method includes moving the tracking target in a step, by the computing system, to a random location on the display; moving the tracking target on the display, by the computing system, from the random location on the display towards the initial location at least until the tracking target crosses the initial location; periodically measuring, by the computing system, user eye position while the user is following the tracking target, and repeating the moving of the tracking target and eye position measurement, by the computing system, a plurality of times. The method also includes analyzing the user eye response measurements, by the computing system, to determine a plurality of quantitative performance measures; and outputting, by the computing system, results of the analysis, wherein the plurality of quantitative performance measurements comprise a cloverleaf as a measure of the user's own idiosyncratic oblique effect that provides a pattern uniquely identifying the user.

The cloverleaf as a measure of the user's own idiosyncratic visual oblique effect provides a baseline for the same user to determine deviation from normal performance for the user; provides a measurement of user performance against a reference population of performance metrics from normal human subjects to determine a deviation from normal for the user; provides a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provides a baseline measurement from the same user for an injury to determine whether the user is faking the injury.

The computer-implemented method further includes comparing, by the computing system, a previous cloverleaf for the user to a current cloverleaf to determine whether the user is improving, deteriorating, or remaining the same.

In another embodiment, a computer-implemented method includes displaying a tracking target, by a computing system, at an initial location on a display for a randomized delay interval. After the randomized delay interval has elapsed, the method includes moving the tracking target in a step, by the computing system, to a random location on the display; moving the tracking target on the display, by the computing system, from the random location on the display towards the initial location at least until the tracking target crosses the initial location; periodically measuring, by the computing system, user eye position while the user is following the tracking target; and repeating the moving of the tracking target and eye position measurement, by the computing system, a plurality of times. The method also includes analyzing the user eye response measurements, by the computing system, to determine a plurality of quantitative performance measures; and outputting, by the computing system, results of the analysis, wherein the plurality of quantitative performance metrics comprise at least one metric for quantifying vigor of pursuit initiation and at least one metric for quantifying a quality of steady-state tracking.

The at least one metric for quantifying the vigor of the pursuit initiation quantifies latency and acceleration and quantifies gain, saccade amplitude, and proportion smooth. The metrics for quantifying vigor of pursuit initiation and quantifying the quality of steady-state tracking provide a baseline for the same user to determine deviation from normal performance for the user; provide a measurement of user performance against a reference population of performance metrics from normal human subjects to determine a deviation from normal for the user; provide a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provide a baseline measurement from the same user for an injury to determine whether the user is faking the injury.

The computer-implemented method further includes comparing, by the computing system, the metrics for quantifying vigor of pursuit initiation and quantifying the quality of steady-state tracking against previous measurements for the user to determine whether the user is improving, deteriorating, or remaining the same.

In yet a further embodiment, a computer-implemented method includes displaying a tracking target, by a computing system, at an initial location on a display for a randomized delay interval. After the randomized delay interval has elapsed, the method includes moving the tracking target in a step, by the computing system, to a random location on the display; moving the tracking target on the display, by the computing system, from the random location on the display towards the initial location at least until the tracking target crosses the initial location; periodically measuring, by the computing system, user eye position while the user is following the tracking target; and repeating the moving of the tracking target and eye position measurement, by the computing system, a plurality of times. The method also includes analyzing the user eye response measurements, by the computing system, to determine a plurality of quantitative performance measures; and outputting, by the computing system, results of the analysis, wherein the plurality of quantitative performance metrics comprise a direction of pursuit response, and a fitting function to describe a shape of a cloverleaf is determined by $$f(\varphi)=1+\alpha\cdot\cos(4(\varphi+\Delta))-\beta\cdot\cos(2(\varphi+\Delta))$$

where $\alpha$ describes a magnitude of cardinal-oblique anisotropy, $\beta$ describes asymmetry between a size of vertical and horizontal lobes, and $\Delta$ describes an orientation of the cloverleaf.

The direction of pursuit response provides a baseline for the same user to determine deviation from normal performance for the user; provides a measurement of user performance against a reference population of performance metrics from normal human subjects to determine a deviation from normal for the user; provides a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provides a baseline measurement from the same user for an injury to determine whether the user is faking the injury.

The computer-implemented method further includes comparing, by the computing system, the direction of pursuit response against previous measurements for the user to determine whether the user is improving, deteriorating, or remaining the same.

In a further embodiment, a system includes a computing system having a display, the computing system configured to display a tracking target on the display, and an eye tracker configured to take periodic measurements of eye position of a user based on the displayed tracking target position, wherein the computing system is further configured to: receive the periodic measurements from the eye tracker, and analyze the received periodic measurements to determine a plurality of quantitative performance measurements and display the eye position measurements and/or results of the analysis, or transmit the received periodic measurements to another computing system that analyzes the received periodic measurements to determine the plurality of quantitative performance measurements, wherein the plurality of quantitative performance measurements includes at least one metric for quantifying vigor of pursuit initiation and at least one metric for quantifying a quality of steady-state tracking.

The plurality of quantitative measurements includes direction tuning, speed tuning, or any combination or subset thereof. The at least one metric for quantifying the vigor of the pursuit initiation quantifies latency and acceleration and quantifies gain, saccade amplitude, and proportion smooth. The metrics for quantifying vigor of pursuit initiation and quantifying the quality of steady-state tracking provide a baseline for the same user to determine deviation from normal performance for the user; provide a measurement of user performance against a reference population of performance metrics from normal human subjects to determine a deviation from normal for the user; provide a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provide a baseline measurement from the same user for an injury to determine whether the user is faking the injury.

The system further includes comparing, by the computing system, the metrics for quantifying vigor of pursuit initiation and quantifying the quality of steady-state tracking against previous measurements for the user to determine whether the user is improving, deteriorating, or remaining the same.

In another embodiment, a system includes a computing system having a display, the computing system configured to display a tracking target on the display and an eye tracker configured to take periodic measurements of eye position of a user based on the displayed tracking target position, wherein the computing system is further configured to: receive the periodic measurements from the eye tracker, and analyze the received periodic measurements to determine a plurality of quantitative performance measurements and display the eye position measurements and/or results of the analysis, or transmit the received periodic measurements to another computing system that analyzes the received periodic measurements to determine the plurality of quantitative performance measurements, wherein the plurality of quantitative performance measurements includes a cloverleaf as a measure of the user's own idiosyncratic oblique effect that provides a pattern uniquely identifying the user.

The cloverleaf as a measure of the user's own idiosyncratic oblique effect provides a baseline for the same user to determine deviation from normal performance for the user; provides a measurement of user performance against a reference population of performance metrics from normal human subjects to determine a deviation from normal for the user; provides a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provides a baseline measurement from the same user for an injury to determine whether the user is faking the injury.

The system further includes comparing, by the computing system, a previous cloverleaf for the user to a current cloverleaf to determine whether the user is improving, deteriorating, or remaining the same.

In yet another embodiment, a computer program embodied on a non-transitory computer-readable medium causes at least one processor to receive a plurality of eye position measurements tracking a user's following of a tracking target over time. The program also analyzes the plurality of eye position measurements to determine a plurality of quantitative metrics, or transmit the plurality of eye position measurements to a remote computing system to analyze the plurality of eye position measurements and determine the plurality of quantitative metrics. Based on the plurality of quantitative metrics, the program provides an indication of whether the user has a brain injury, whether the user has a disease, whether the user is faking an injury, whether the user is intoxicated, or any combination thereof, wherein the plurality of quantitative performance metrics comprise a direction of pursuit response, and a fitting function to describe a shape of a cloverleaf is determined by $$f(\varphi)=1+\alpha \cdot \cos(4(\varphi+\Delta))-\beta \cdot \cos(2(\varphi+\Delta))$$

where $\alpha$ describes a magnitude of cardinal-oblique anisotropy, $\beta$ describes asymmetry between a size of vertical and horizontal lobes, and $\Delta$ describes an orientation of the cloverleaf.

The direction of pursuit response provides a baseline for the same user to determine deviation from normal performance for the user; provides a measurement of user performance against a reference population of performance metrics from normal human subjects to determine a deviation from normal for the user; provides a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provides a baseline measurement from the same user for an injury to determine whether the user is faking the injury.

The computer program further includes comparing, by the computing system, the direction of pursuit response against previous measurements for the user to determine whether the user is improving, deteriorating, or remaining the same.

The computer program further includes comparing the frequency response of the vestibular-driven ocular response (i.e., the vestibulo-ocular reflex at multiple viewing distances to distinguish distance-dependent otolith and distance-independent canal responses) against previous measurements for the user to determine whether the user is improving, deteriorating, or remaining the same as well as postural and arm stability measures of vestibule-spinal function.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 1A illustrates graphs of Comprehensive Oculometric Behavioral Response Assessment (COBRA) oculometric measurements for a typical control subject, according to some embodiments.

FIG. 1B illustrates graphs of COBRA oculometric measurements for a TBI subject, according to some embodiments.

FIG. 3 is a scatterplot illustrating a three-dimensional subspace of a ten-dimensional dataset for control (filled circles) and TBI subjects (open circles), according to some embodiments.

DETAILED DESCRIPTION OF THE EMBODIMENTS

Figure 2:
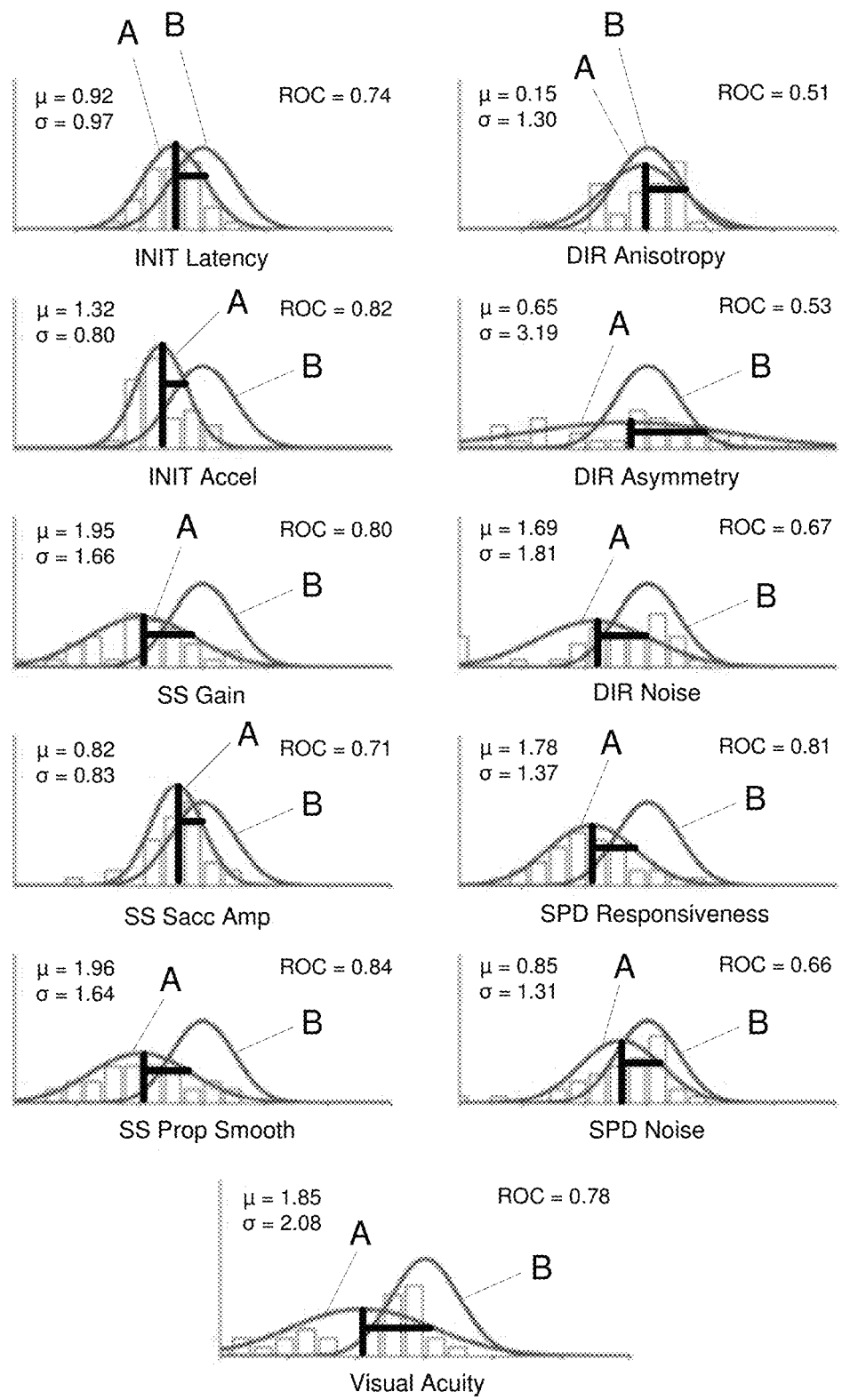
FIG. 2 illustrates graphs of the distributions of all ten COBRA metrics, as well as static visual acuity, according to some embodiments.

Certain embodiments of the present invention improves the capability of the original Comprehensive Oculomotor Behavioral Response Assessment (COBRA) system by harnessing multimodal 3D imaging technologies for robust, calibration free, head and eye tracking to allow for visual, vestibular, and oculomotor assessment of human neural health and performance.

Some embodiments of the invention measure head movement assess vestibular function. These embodiments distinguish eye movements in the head from those caused by head movement.

Some embodiments of the invention provide the advantages of being a small, lightweight, low-power, easy-to-use system that does not require repeated calibration, and could be instantiated as a hand-held device that is immune to head-movement artifacts and appropriate for operational deployment. Other objectives is to improve current visual and visuomotor testing to include an assessment of vestibular function.

Some embodiments of the present invention are configured to diagnose a condition by deriving a sensitive indicator of the likelihood of a particular disease or injury state based on results of an eye-movement assessment test that includes an appropriately randomized, radial tracking task together with a broad set of oculometric measures. The oculometric measures may be combined to yield the sensitive overall indicator of sensorimotor functional status. More specifically, the oculometric measures may be vectorized to help diagnose both the type of disease, injury, or impairment and the extent thereof.

Based on experimentation, search templates for TBI, diseases, and other sources of impairments may be derived using data, such as Comprehensive Oculometric Behavioral Response Assessment (COBRA) expressed in a 10-dimensional space of metrics (or any n-dimensional space without deviating from the scope of the invention). More specifically, individuals with a certain condition may be tested and an "average" representation across such a population may be developed for their condition. The severity of the TBI, disease, or impairment for an individual can then be quantified as single scalar value. This solves the problem of converting a complex qualitative pattern of deficits (e.g., prolonged latencies, sluggish accelerations, reduced gain, elevated direction noise, etc.) expressed in the native units of the measurements (e.g., milliseconds (ms), deg/s^2, etc.) into a single metric based on the combination of standard normalized units. Used in combination with a reference database from a population of normal (non-impaired) subjects, the "impairment vector" (a form of search template) quantitatively characterizes a complex pattern of symptoms across a population of similarly affected subjects (e.g., suffering from the same disease or injury) and the "impairment indices" computed from individuals using these "impairment vectors" quantify the severity of a disorder, or lack thereof, consistent with the candidate impairment.

For COBRA (or any oculometric technology like COBRA) to screen for neurological signs of disease and injury, a characteristic set of signs should be derived for each potential disease or injury of interest. Some embodiments give a recipe to compute this characteristic set of signs as well as the specific vector for traumatic brain injury (i.e., the "TBI vector"). The impairment vector or search template characterizes the disorder quantitatively, and the impairment indices derived from an individual's data quantify how severe the individual's disorder is.

A benefit of some embodiments is that an n-dimensional space of metrics may be reduced to a vector, which has both a direction and an amplitude. COBRA is currently a 10-dimensional space, but any other number of metrics may be used without deviating from the scope of the invention. By comparing the vector of a tested individual to search templates (i.e., average or characteristic vectors) for different TBI types, diseases, and/or impairments (e.g., alcohol or drug intoxication, sleep deprivation, etc.), it can be discerned with a reasonable probability which condition or conditions an individual is likely to have, as well as how severe the individual's condition is. Generally, the data from individuals with a given condition will point in the same basic direction and amplitude. This enables condition and severity identification for a previously untested individual whose condition may be unknown.

The vectors or search templates for different TBI, diseases, and impairments can be used to determine the likelihood of that impairment. In some cases, conditions that are not necessarily intuitive as being detectable via visual testing (e.g., diabetes) may be diagnosed. The larger the projection of an individual's oculomotor performance vector onto a given condition's impairment vector, the higher the likelihood that the individual ha the condition associated with that impairment vector.

Some embodiments have advantages over conventional TBI, disease, and impairment detection technologies. Indeed, some embodiments change diagnostic technology from merely detecting whether an impairment exists to determining whether the impairment fits the complex multi-dimensional pattern associated with a specific condition. How the individual deviates from a general population with a condition may also be measured. This provides a discriminatory capability that can characterize the deficit (i.e., aid in actual diagnosis) as opposed to merely detecting it (i.e., determine that the person is suffering from something).

Per the above, the direction and amplitude of the individual's vector may define the "flavor" of the condition. For instance, the individual's data may project onto a specific impairment vector (e.g., the glaucoma vector) to yield an impairment index of X, suggesting an elevated likelihood of glaucoma. With enough dimensions, a range of individual conditions may be readily distinguishable from one another by yielding lower values of the indices associated with projections onto the impairment vector related to other conditions (e.g., TBI, sleep deprivation, retinitis pigmentosa, etc.). Additionally or alternatively, some embodiments may help to focus testing and speed diagnosis. For instance, if an individual maps X to glaucoma, but further testing by an ophthalmologist reveals that this is not the actual condition, the ophthalmologist can move to additional tests for the next most likely condition (i.e., with the next highest impairment index below X), and the next, and so on, until the actual condition is properly diagnosed.

Another advantage of some embodiments is that non-obvious conditions may be detected and identified very early in their progression, increasing the chance that the progression can be reversed, stopped, or slowed. By the time imaging reveals a condition, it is usually quite severe. Furthermore, in certain environments where multiple causes for a deficit are possible, the true cause can be determined. For instance, where a soldier has been subjected to a blast and has also been up for 48 straight hours, it can be determined which of these causes (or both) is the actual culprit for his or her deficits. Sleep deprivation looks significantly different from TBI due to blast trauma. Trucking companies could also employ such a test to clear their drivers for operation. While trucking companies themselves may be hesitant to spend the potential additional time and cost, insurance companies may drive them to do so. Also, law enforcement could use certain embodiments for testing in the field to determine how intoxicated/impaired a given individual is due to marijuana or alcohol, for instance, or whether their impairment results from another condition (e.g., sleep deprivation).

Per the above, some embodiments employ COBRA that derives various quantitative oculometrics from the test, which are then used for the assessment. Following calibration, subjects participate in an eye-movement tracking task including a certain number of trials (e.g., 180 trials). A chin and forehead rest may be used for head stabilization. On each trial in some embodiments, a radial version of Rashbass step-ramp motion is then displayed, whereby the target makes a step in a random direction from a central fixation location, then moved back through the original location at a constant velocity (e.g., 16-24 deg/s). The speed, direction, onset-timing, and duration of target motion may be independently randomized to promote uniform distribution of attention across space, time, and direction and to defeat strategies using anticipatory or predictive eye movements.

Field-Deployable Neurological Assessment Tool

Certain embodiments of the present invention improves the capability of the original Comprehensive Oculomotor Behavioral Response Assessment (COBRA) system by harnessing multimodal 3D imaging technologies for robust, calibration free, head and eye tracking to allow for visual, vestibular, and oculomotor assessment of human neural health and performance.

Some embodiments of the invention measure head movement assess vestibular function. These embodiments distinguish eye movements in the head from those caused by head movement.

Some embodiments of the invention provide the advantages of being a small, lightweight, low-power, easy-to-use system that does not require repeated calibration, and could be instantiated as a hand-held device that is immune to head-movement artifacts and appropriate for operational deployment. Other objectives is to improve current visual and visuomotor testing to include an assessment of vestibular function.

Embodiments of the invention include three separate functional components: a tracker and display subsystem for data collection; an analyzer subsystem for data analysis; and a visualizer subsystem for database management and visualization.

In some embodiments, the tracker and display sub-system includes at least a pair of cameras for stereo 3D imaging, including a suite of 3D imaging systems that are active or passive, such as N-grouped camera systems, Time-of-Flight Camera systems, LIDAR, Infra-Red Illuminator/Camera, Integrated/Disparate Light Sensing & spectral analysis, 3D Head/Object modeling systems, synchronized with a 2D/3D high-speed/resolution audio-visual display system. According to embodiments, the audio-visual display system has at least 90 Hz visual temporal resolution, 1K HD visual spatial resolution, ability to provide spatial auditory feedback or cues, and ability to detect a trigger from the user.

In some embodiments, the analyzer sub-system for data analysis identifies users through biometric recognition, including face, iris, or retinal recognition. In some embodiments, the analyzer sub-system is processes the tracker data stream, either in real time or by off-line analysis of video streams, to determine a 6 degrees-of-freedom (dof) head position in the world as $X_h$, $Y_h$, $Z_h$, $Yaw_h$, $Pitch_h$, $Roll_h$ with respect to the system anchor coordinates. In some examples, the tracker data streams are at least at 30 Hz. The analyzer sub-system also processes the tracker data stream to determine a 3 dof eye position in the head as $X_e$, $Y_e$, and $R_e$ with respect to the head position coordinates. In some embodiments, the tracker data stream for determining eye position are at least at 120 Hz, but preferably 240 Hz. In some embodiments, at least a head position and an eye position are determined for each frame of data from the tracker data stream. The system then uses the COBRA visual analytics on the stream of head position and eye position data to generate a plurality of oculometrics of dynamic visual function and visuomotor control. The system also uses another suite of COBRA vestibular analytics to generate a plurality of oculometrics of vestibular function, which measures of yaw and pitch vestibulo-ocular reflexes, for both the canal and otolith components separately.

In some embodiments, the visualizer subsystem, including database management sub-system and a visualization sub-system that stores and organizes all COBRA data. In some embodiments, the data is organized by subject, run, or treatment. The system allows visualization of any subject in comparison with his or her previous or baseline data, or with that of a matched cohort to allow for rapid and objective operational decisions related to readiness to perform or to seek medical evaluation or treatment.

Some embodiments of the system use 3D imaging and head modeling to record head and eye-movement data with respect to a set of identified and inter-related coordinate systems from the multiple input devices. The system fuses the multiple pieces of head/eye information from multiple imaging systems for maximal robustness, accuracy, and precision without the need for a calibration run. This approach also allows for clean segregation of head and eye movement data.

The field-deployable system provides advantages over approaches where the head was imperfectly stabilized using a chin rest. Embodiments of the invention virtually stabilizes the head in real time because head position is monitored in 6 dof at least at 30 Hz such that the eye-movement data is appropriately and automatically corrected or updated for head motion on a sample-by-sample basis. In this novel approach, the subject's head is free of a chin rest while the system generates eye-movement data free of head movement artifacts. Instead of a display that is fixed in a rigid stand, the system's visual display is virtually stabilized when it generates the COBRA stimulus set for its polar Rashbass-like task and characterizes input-output functions of human visual performance (as a function of direction and speed), As the relative position/orientation of the head and display is monitored in 6 dof in real time at least at 30 Hz, the display can be appropriately corrected or updated for display position or orientation, and for head postural changes, on a trial-by-trial basis. This allows the display to be hand-held without the need for a stand.

Some embodiments of the invention allows the ability to assess vestibular function, which would not be possible in a system where the head was fixed on a chin rest and head stand. Vestibulo-ocular reflex (VOR) is a reflex, where activation of the vestibular system in the inner ear causes eye movement. According to some embodiments, the system records head position and eye position as the user executes particular movements of their head to generate vestibular stimuli. In some embodiments, the user can be responding to auditory feedback or cues, such as tones, beeps, or verbal instructions, to move one's head. In some embodiments, the head positions and eye positions are recorded to generate multiple frequencies (e.g., a Bode Plot). The user can hold the display at multiple viewing distances, thus not only allowing the vestibulo-ocular reflex to be measured, but also allowing the canal and otolith components to be dissociated for more refined diagnostics.

In an example embodiment of the invention, the system includes an Apple iPad Pro 12.9" (2018 Edition) to provide the display and user-facing "selfie" camera and LIDAR systems. The iPad device's front-facing camera provides a high fidelity head tracking with 6 dof and 60-Hz sampling rate, using its high-resolution head model for tracking and face recognition. In some embodiments, an iPhone XS (2018 Edition) is rigidly attached to the iPad, where a rear-facing stereo camera system is turned toward the user to perform eye tracking at 240 Hz sampling rate. In some embodiments, head tracking is also performed using the iPhone's stereo images and fiduciary points to map the images back into the iPad camera coordinates. Because the coordinate transformations from camera to camera and head to head use straight-forward linear algebra solutions, and because head motion is very low-frequency band limited, the eye-in-the-head signal from the 240 Hz eye tracker can be combined with head-in-the world signal from the 60-Hz head tracker to yield both cyclopean gaze angle in the head and gaze point in the world (at a 240 Hz sampling rate) for analysis using the original COBRA visual assessment algorithms as well as the novel vestibular assessment algorithms.

While some embodiments of the invention are described herein with reference to Apple iPad and Apple iPad products, it is understood that other devices with the described hardware and capabilities may be used with such embodiments without departing from the scope and spirit of the invention.

Embodiments of the invention provide the following advantages:

1. No need for calibration before each run. As the system uses full 6 dof 3D imaging and head-modeling systems for head and eye tracking, there is no need for brute force calibration needed to get 2D eye position information from a camera into 3D angular measures of yaw and pitch (in-head coordinates). In some embodiments, the system measures all of the necessary variables, including but not limited to inter-ocular distance, viewing distance, head position and orientation, to generate gaze-in-the-head angles and gaze point in the world without any calibration. Even head mounted displays do not avoid this problem as individual variation in inter-ocular distance and eye depth in the orbit can generate pronounced artifacts in such systems, in addition to field of view, display resolution, and operational penalties. Calibration typically take between 1 and 5 minutes, so embodiments of the invention provides the advantage of saving time, which is essential in operational settings.

2. No need for a chin rest or a display stand. Because head position/orientation and display position/orientation are monitored in essentially real time, the stimuli, and head or eye movement data can be updated in real time as limited by the sampling rate, or as appropriate (virtual chin rest and stand). With these embodiments, there is no need for a table, stand, or even a chair, as COBRA testing can be taking using a hand-held device, even while standing. Furthermore, using the proposed iPad/iPhone embodiment, the device would be light weight and low power, and thus suitable for operational use.

3. No need for an operator, infrastructure, or external power. The mobile device (e.g., iPad/iPhone) instantiation allows the user to run the system by themselves, even in settings without infrastructure or power, such as in spaceflight, battlefield, or sports field deployments.

Embodiments of the invention can be used to satisfy NASA's need for reliable non-invasive tools to determine readiness-to-perform during and after exposure to challenging environments (e.g., high/low G, high CO2, low O2, vibration, etc.). Additionally, embodiments of the invention can be used in a wide range of operational (e.g., aeronautics, space, military), sports, and clinical settings as a powerful non-invasive method for detecting and characterizing mild neural impairment that could affect performance (increase risk to mission or for the team) as well as individual health and safety.

Given its expanded potential as a visual, vestibular, and oculomotor test battery and the new potential to develop a portable, hand-held, self-powered, easy-to-use device, such an "iCOBRA" device could become a standard neural/neurological assessment tool for both operational decision making and medical practice.

Figure 6:
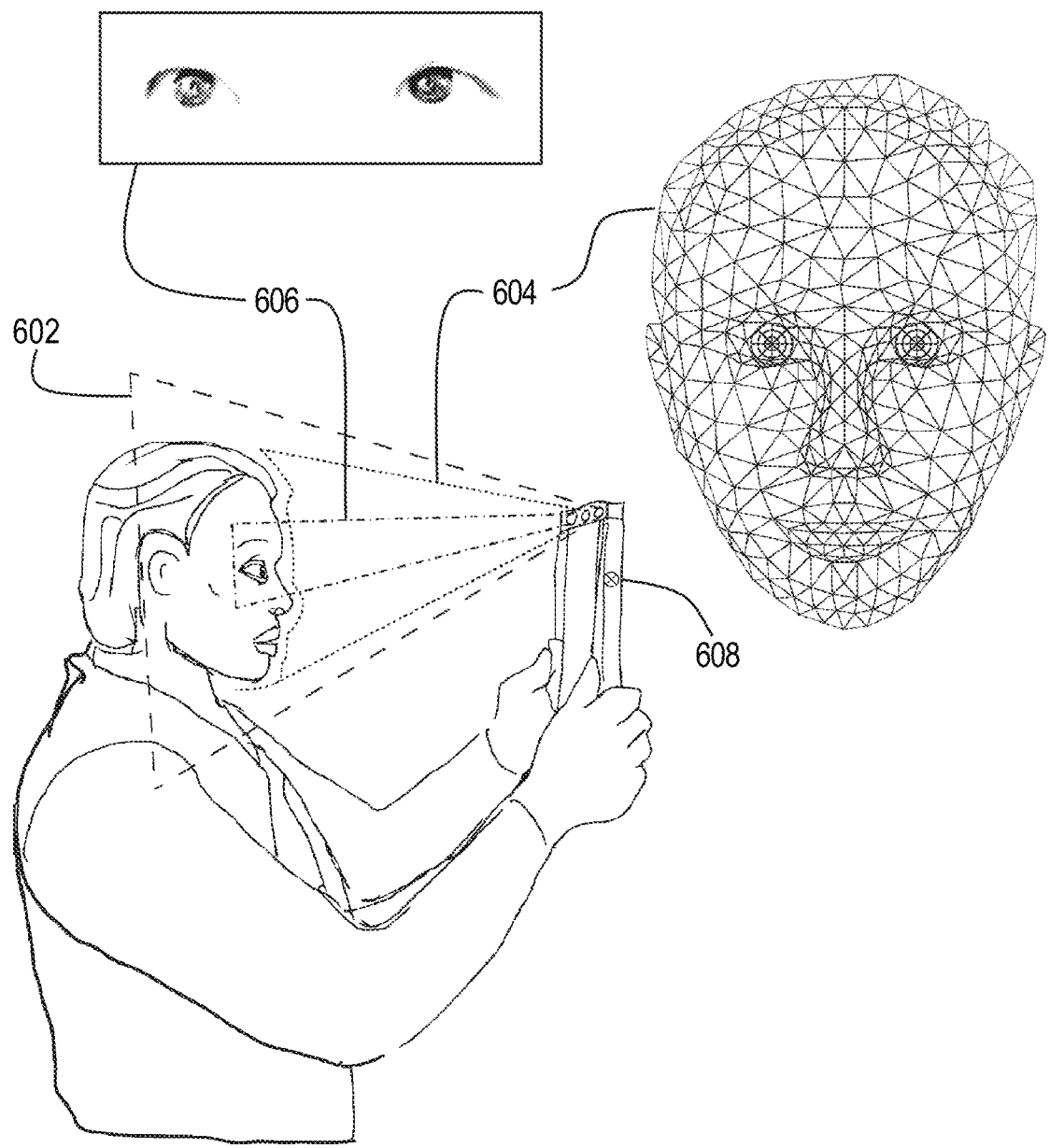
FIG. 6 is a diagram illustrating the use of a hand-held field-deployable neurological assessment tool for performance readiness and telemedicine, according to some embodiments.

FIG. 6 is a diagram illustrating the use of a hand-held field-deployable neurological assessment tool for performance readiness and telemedicine, according to some embodiments. Device 608 includes at least three cameras 602, 604, and 606 for capturing fields-of-view. Camera 602 is a primary optical camera capturing head data. Camera 604 is a 3D camera system capable of capturing head and eye data in 6 dof. Camera 606 is a high framerate camera that is configured to capture eye data. In some embodiments, the camera is configured to capture eye data in isolation. In some embodiments, the device includes an inertial measurement unit 608, such as a accelerometer, gyroscope, or magnetometer, for capturing device motion information at multiple degrees of freedom.

Figure 7:
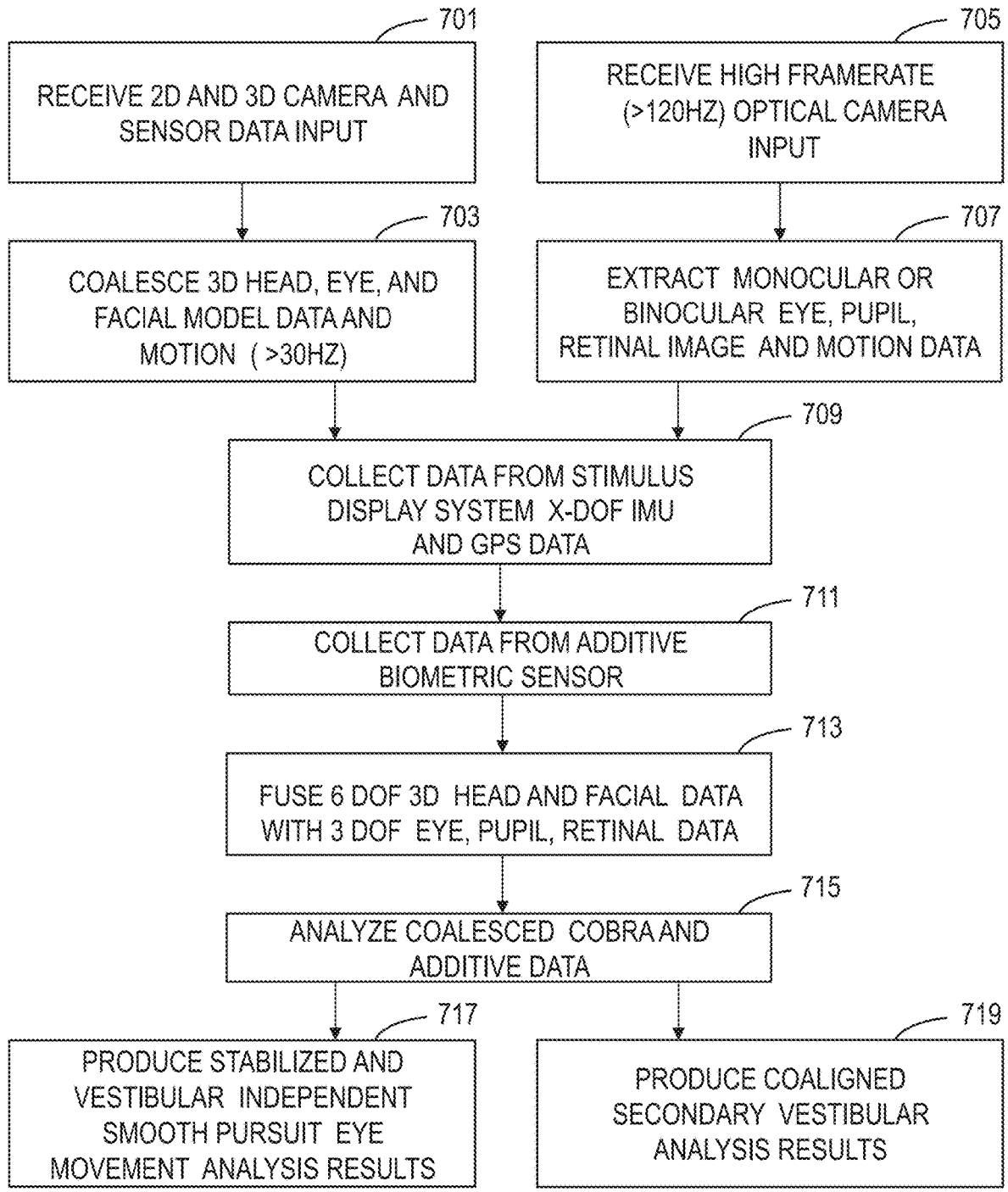
FIG. 7 is a flow diagram illustrating a method for neurological assessment using a field-deployable assessment tool, according to some embodiments.

FIG. 7 is a flow diagram illustrating a method of producing oculometries of visuomotor control and vestibulo-ocular reflex, according to some embodiments. At step 701, the system receives 2D and 3D camera and sensor input for capturing a tracker data stream for determining head position in the world. In some embodiments, the camera inputs include single or multiple 2D optical cameras, such as visible light, infrared, ultraviolet cameras. Camera inputs may also include inputs from 3D sources, such as LIDAR, time-of-flight, stereo camera pairs, or depth sensing cameras. At step 703, the system coalesces 3D head, eye, and facial model data and motion. In some embodiments, tracker data stream for determining head position is sampled at a frame rate of at least 30 Hz. At step 705, the system receives high framerate optical input for capturing a tracker data stream for determining eye position within the head, for example, from one or more optical cameras. At step 707, the system extracts monocular or binocular eye, pupil, and retinal image and motion data. As shown in the flow diagram, according to some embodiments, the steps 701 and 703 proceed simultaneously with steps 705 and 707, and continuously for each new sampled frame captured.

At step 709, data is collected from the portable device's inertial measurement unit (IMU) and GPS data to determine the movement of the device in the user's hands. IMU input includes input from devices such as 3-axis gyroscope, 3-axis compass, or a 3-axis accelerometer. GPS input includes latitude, longitude, and spatial temporal motion.

At step 711, data is further collected by an additive biometric sensor. Examples of biometric sensor input include heart rate, EKG, galvanic skin response, temperature sensor, blood pressure, blood sugar, and cellular respiration.

At step 713, the 6 dof head and facial data from step 703 is fused with 3 dof eye, pupil, and retinal data from step 707. At step 705, the fused data can be analyzed using the techniques described above, or in combination with the additive biometric data, to produce stabilized and vestibular-independent smooth pursuit eye movement analysis results, or to produce co-aligned secondary vestibular analysis results.

TBI and Experimental Control Populations

In an experiment that was conducted, 34 TBI subjects were recruited from local medical facilities and brain injury rehabilitation centers who met the following requirements: (i) security rules allowed them access to NASA Ames Research Center (US citizen); (ii) aged between 18-70 years old; (iii) self-reported nonpenetrating impact trauma to the head, verified using the Ohio State University TBI Identification Method; (iv) able to make their own medical decisions and sign informed consent forms; (v) able to sit still for 20 minutes, fixate for several seconds at a time and track with the left eye while keeping their head still; (vi) able to sit, stand, and walk without assistance; and (vii) better than 20/200 visual acuity. Subjects completed a survey to document their age, gender, whether they needed glasses or contacts, when they were diagnosed, when they were injured, and a self-reported assessment of the severity of their current condition, with 1 being "little to no residual injury" and 10 being "completely disabled". The causes of injuries sustained by this TBI population varied in both type and severity, including: unspecified injuries (5 subjects), motor vehicle accidents (18 subjects), falls (1 subject), bicycle or skateboarding accidents (8 subjects), and assault (2 subjects). Of the 25 TBI subjects who reported their TBI on the mild-moderate-severe scale, 2 reported mild TBI, 5 reported moderate TBI, 3 reported moderate-to-severe TBI, and 15 reported severe TBI.

The subject population reported loss of consciousness (LOC) ranging in duration from no LOC to two months in a coma. Using the durations provided by the Ohio State University TBI Identification Method, 2 subjects reported no LOC, 7 subjects reported LOC less than 30 minutes, 1 subject reported LOC between 30 minutes and 24 hours, and 24 subjects reported LOC greater than 24 hours. The Freiburg Visual Acuity Test was used to measure binocular visual acuity. For the 34-subject TBI population (21 males, 13 females) ranging in age from 20 to 61 years ($10^{th}$ percentile: 23 years, $25^{th}$ percentile: 26 years, $50^{th}$ percentile: 34 years, $75^{th}$ percentile: 49 years, $90^{th}$ percentile: 57 years), the mean time since injury was 9.1 years (range: 6.9 months to 32.2 years; $10^{th}$ percentile: 1.0 year, $25^{th}$ percentile: 3.6 years, $50^{th}$ percentile: 6.1 years, $75^{th}$ percentile: 16.1 years, $90^{th}$ percentile: 19.0 years) and the mean self-reported severity level was 3.3 (range: 1-7), with static visual acuity ranging from −0.28 to 0.44 (median: −0.08).

The 41-subject control population (22 males, 19 females) ranging in age from 20 to 56 years ($10^{th}$ percentile: 22 years, $25^{th}$ percentile: 24 years, $50^{th}$ percentile: 27 years, $75^{th}$ percentile: 35 years, $90^{th}$ percentile: 51 years) had static visual acuity ranging from −0.29 to 0.44 (median: −0.20). Although the age distribution of control subjects was skewed toward younger ages and the distribution of ages of TBI subjects was more uniform, the difference in age between the two populations was only borderline significant (p=0.052, Wilcoxon rank sum test). Although the control population was not screened for history of brain injury, any unknown injuries in the control population would only serve to underestimate the TBI detectability using COBRA.

TBI Vector and TBI Impairment Index

To characterize the TBI-related signs present in the task, a previously-described baseline data set was used as a normative standard. First, a set of ten measurements from each subject was considered in their native units (e.g., ms, deg, deg/s$^2$, etc.) as a raw COBRA vector. The raw measurements were then converted into z-values (units of standard deviation to allow for comparison across the disparate dimensions) relative to the control data set by subtracting the median and scaling by the estimated standard deviation:

$$\omega = \frac{RAW - CONTROL_{50th}}{\sigma} \quad (1)$$

where $$\sigma = \frac{(CONTROL_{75th} - CONTROL_{25th})}{2 \cdot \Phi^{-1}(0.75)}$$

and $\Phi^{-1}$ is the inverse of the normal cumulative distribution function. For the steady-state gain metric, an arcsin correction was applied to de-skew the raw data. Lastly, the sign for the latency, speed noise, saccadic amplitude, and direction noise metrics was flipped so that negative values indicate impairment. Normalized metrics ($\omega$) with higher values correspond to faster, quicker, smoother, higher-gain, and more accurate tracking. Lower values correspond to slower, less accurate movements with larger and more frequent saccades. For these analyses, a 10-element COBRA vector of normalized metrics was used:

$$COBRA = \begin{bmatrix} \omega_{INIT\ latency} \\ \omega_{INIT\ accel} \\ \omega_{SS\ gain} \\ \omega_{SS\ sacc\ amp} \\ \omega_{SS\ props\ mooth} \\ \omega_{DIR\ anisotropy} \\ \omega_{DIR\ assymetry} \\ \omega_{DIR\ noise} \\ \omega_{SPD\ responsivness} \\ \omega_{SPD\ noise} \end{bmatrix} \quad (2)$$

In COBRA, INIT is initialization, DIR is direction tuning, SS is steady-state tracking, and SPD is speed tuning. However, direction-tuning anisotropy and asymmetry metrics were excluded when the level of direction noise exceeded 25° (4 of 34 TBI subjects) because the fits that yield these two metrics became numerically unstable and unreliable.

To characterize TBI-related oculomotor signs, COBRA vectors were averaged across the TBI population to yield a TBI vector:

$$TBI = \sum_{i=1}^{n} \left( \frac{COBRA_i}{n} \right) \quad (3)$$

Where n is the number of TBI subjects. Because the COBRA vectors are "normalized", each element of the TBI vector gives the distance (in standard deviation units or z-values) between the average TBI subject and the average of the control population, defined as the origin. For example, if there were no effect for a given metric, the mean of the TBI population would fall near zero along that axis. While more complicated formulations (e.g., a vector based on signal-to-noise) may afford incrementally-better statistical power, the most intuitive definition of the TBI vector was used for this example.

To quantify the scalar magnitude of the functional impairment along the TBI vector, the dot product was taken between an individual's COBRA vector and the TBI vector to yield a cross-correlation-based scalar metric:

$$TBI\ \text{Impairment Index} = \frac{COBRA * TBI}{SCALING\ FACTOR} \quad (4)$$

$$SCALING\ FACTOR = \|CHOL(COV(CONTROL)) * TBI'\|$$

The scaling factor in the denominator ensures a standard normal distribution of TBI impairment indices for the control population and scales the resulting index in standard deviation units of the control population. CHOL is the Cholesky Decomposition, COV(CONTROL) is the covariance matrix created by the entire set of COBRA vectors of the control population, and TBI' is the transpose of the TBI vector.

Results

The oculometric approach applied in this example yields a ten-dimensional summary of an individual's performance on the tracking task, for both control and TBI subjects. FIGS. 1A and 1B illustrate graphs 100 of COBRA oculometric measurements for a typical control subject and a TBI subject, respectively, according to an embodiment of the present invention. Histograms in the left-hand columns of both FIGS. 1A and 1B plot across-trial measurements of standard measures of pursuit performance. Direction-tuning and speed-tuning measurements of visual motion processing are shown in the right-hand columns. Pursuit initiation (INIT) measurements yield a skewed distribution of latencies and a quasi-normal distribution of accelerations. Steady-state (SS) tracking measurements (400 to 700 ms after motion onset) include: pursuit gain (ratio of eye speed to target speed), the average amplitude of saccades, and the proportion of total eye displacement that was smooth. The direction-tuning (DIR) plot shows pursuit direction as a function of target direction for each trial. The insets 102, 104 illustrate the "cloverleaf" direction-gain anisotropy and asymmetry 106 (gray line) referenced to the circle of unity gain (thin black line).

Qualitative comparison of FIGS. 1A and 1B captures some of the functional consequences of TBI-related tissue damage seen in the raw data. The control and TBI subjects shown highlight typical TBI-related oculomotor tracking deficits: longer latency, lower initial acceleration, lower steady-state gain, larger saccades, and a lower proportion of smooth movement. Obvious impairments in this TBI subject include high direction noise, large distortion in the direction-tuning function and low speed-tuning responsiveness. Although these two subjects are drawn from populations with substantial across-subject variance, the overall results demonstrate degraded tracking for the TBI population. See Table 1 below.

histogram plots the values for the 34-subject TBI population. Inset into each set of axes are the mean and standard deviation for each of the TBI population's metrics, and the Receiver Operating Characteristic (ROC) curve area between the two distributions, which quantifies the ability of an ideal observer to discriminate one sample at random from one of the two distributions.

The TBI vector (see FIG. 3) is defined by the set of ten mean ($\mu$) values. More specifically, FIG. 3 illustrates a perspective two-dimensional (2D) rendering of a three-dimensional (3D) subspace showing the TBI vector in this subspace and the population of normal and injured subjects. It is not possible to graph the full TBI vector in a ten-dimensional (10D) space on 2D paper. However, the salient point is clear from the plot of the 3D subspace. TBI patients deviate systematically from normal along a particular direction in both this 3D subspace and in the 10D space that cannot be fully shown visually. Furthermore, this illustrates the problem of dealing with the full 10D (or more, in some embodiments) space of raw oculometric measures and motivates the need for extracting a single scalar measure from the full 10D (or more) space that still captures the critical information about how much any individual's 10D (or more) COBRA vector deviates from normal along the 10D (or more) direction defined by the TBI vector (i.e., a single measure that indicates that the person is likely to be within the TBI population). This was a motivation for inventing the "impairment index."

TABLE 1

DISTRIBUTIONS OF COBRA OCULOMETRICS FOR CONTROL AND TBI POPULATIONS

| | Control Population | | | | TBI Population | | | |
|---|---|---|---|---|---|---|---|---|
| | $25^{th}$ | $50^{th}$ | $75^{th}$ | $\sigma$ | $25^{th}$ | $50^{th}$ | $75^{th}$ | $\sigma$ |
| INIT Latency (ms) | 176 | 180 | 185 | 7 | 182 | 187 | 191 | 7 |
| INIT acceleration (deg/s$^2$) | 92 | 124 | 143 | 38 | 52 | 69 | 93 | 30 |
| SS Gain | 0.75 | 0.82 | 0.86 | 0.08 | 0.52 | 0.66 | 0.74 | 0.16 |
| SS Sacc. Amp. (deg) | 1.96 | 2.29 | 2.69 | 0.54 | 2.37 | 2.65 | 2.98 | 0.45 |
| SS Prop Smooth | 0.62 | 0.67 | 0.75 | 0.09 | 0.39 | 0.48 | 0.59 | 0.15 |
| DIR Anisotropy | 0.27 | 0.37 | 0.48 | 0.16 | 0.23 | 0.36 | 0.52 | 0.21 |
| DIR Asymmetry | 0.05 | 0.10 | 0.20 | 0.11 | −0.07 | 0.11 | 0.45 | 0.39 |
| DIR Noise (deg) | 6.62 | 8.66 | 11.10 | 3.32 | 7.65 | 11.78 | 15.75 | 6.01 |
| SPD Responsiveness | 0.42 | 0.55 | 0.65 | 0.17 | 0.10 | 0.22 | 0.41 | 0.23 |
| SPD Noise (deg/s) | 2.56 | 3.43 | 4.07 | 1.12 | 3.18 | 3.79 | 5.16 | 1.46 |
| Visual Acuity (LogMAR) | −0.23 | −0.20 | −0.11 | 0.09 | −0.15 | −0.08 | 0.13 | 0.21 |

"Log MAR" is the Logarithm of the Minimum Angle of Resolution. For each population, Table 1 gives the $25^{th}$, $50^{th}$, and $75^{th}$ percentile values for the ten oculometrics measured by the task, as well as the estimated standard deviation $\sigma$. For subjects with high levels of directional noise observed in the TBI population (25° or greater, 4 participants), the fitted anisotropy and asymmetry of the direction-tuning function (see FIGS. 1A and 1B) became unstable and have been omitted from the reported distributions (bold typeface cells).

To characterize the set of TBI-related deficits, the data was first normalized by the across-subject variance in the control population and then compared the distributions of values for TBI and control populations using an across-subject paradigm. Graphs 200 of FIG. 2 illustrate the distributions of all ten COBRA metrics and static visual acuity. Each graph plots the Gaussian fits to the distributions for control (B) and TBI (A) populations. The black unfilled Considered separately, significant decrements were observed in the TBI population for six of the ten metrics (for initial acceleration, steady-state gain, steady-state proportion smooth, speed responsiveness, and steady-state saccade amplitude). A significantly lower static visual acuity was also observed for the TBI subjects (median: −0.08 Log MAR, 20/16 Snellen; range: −0.28 to 0.44, 20/11 to 20/55) with respect to the control population (median: −0.20 Log MAR, 20/13 Snellen; range: −0.29 to 0.44, 20/10 to 20/55), similar to previous reports. Overall, visual acuity was not significantly correlated with self-reported TBI severity (p=0.127, r=−0.20, Pearson's R) so acuity problems are not a significant factor in their self-reported impairment.

To evaluate the ability of the data to identify the TBI status of the subject without the benefit of individual baselines, two techniques from signal-detection theory were applied in an across-subject paradigm. First, the TBI vector (see TBI vector 310 in scatterplot 300 of FIG. 3) was defined to be the across-observer average of COBRA vectors for the TBI population, indicated by the gray vertical lines in FIG. 2. Scatterplot 300 shows a three-dimensional subspace of the ten-dimensional dataset for control subjects (black filled circles) and TBI subjects (black unfilled circles). A "TBI vector" (i.e., solid gray vector 310) was defined to point from the origin to the average across the TBI population. Two TBI data points fall right at the tip of TBI vector 310 and are difficult to segment from the arrowhead—one can be seen to occlude a nearby control data point, and the other can be seen as a gray fringe occluded by the same control data point. As TBI vector 310 gives the typical pattern of oculomotor signs observed with TBI subjects, the projection of any given subject's vector along the TBI vector, the subject's TBI impairment index, is an overall scalar measure of the severity of their impairment, scaled to the unit variance of the control population.

Figure 4A:
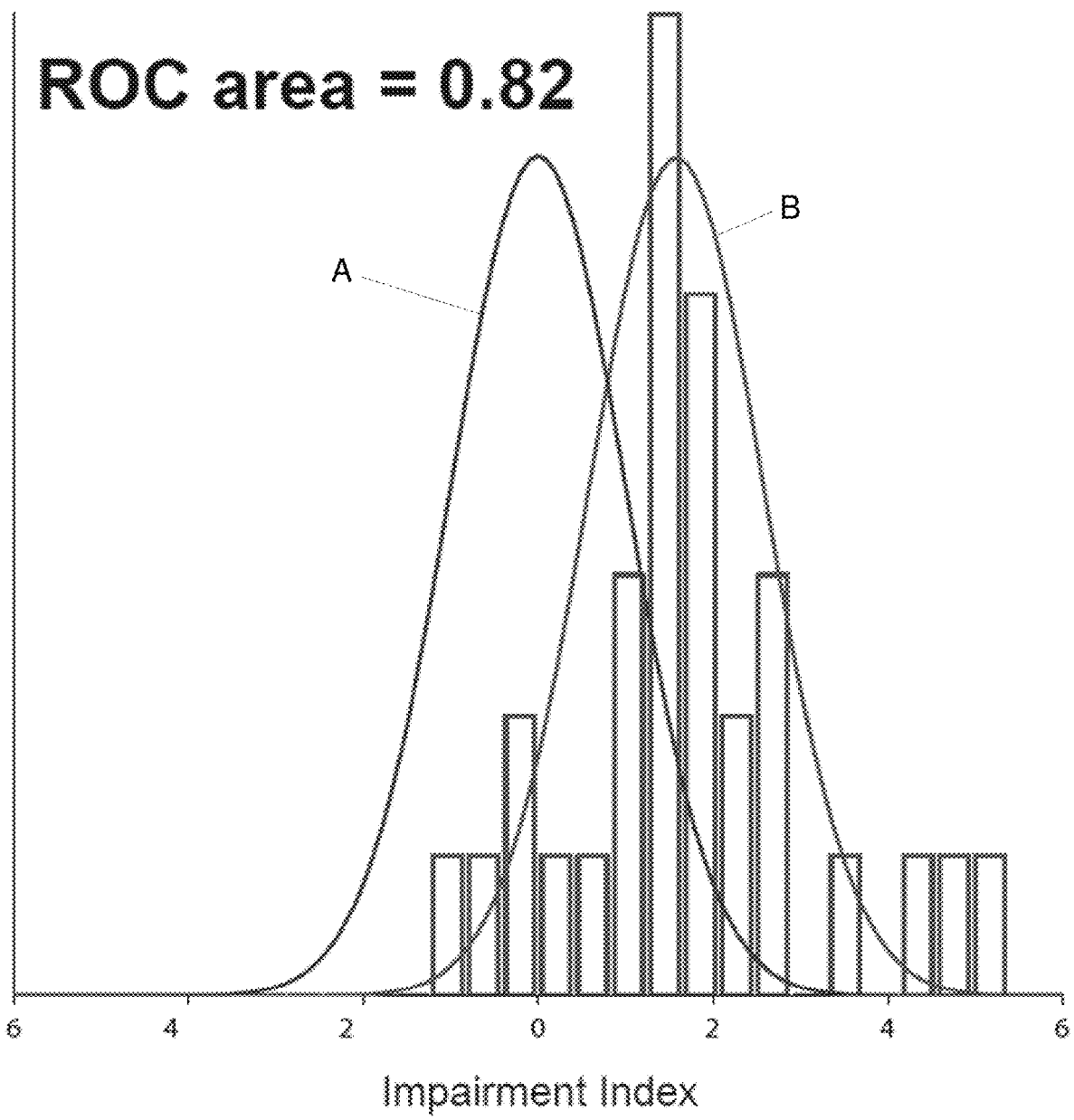
FIG. 4A is a histogram illustrating TBI impairment indices, according to some embodiments.
Figure 4B:
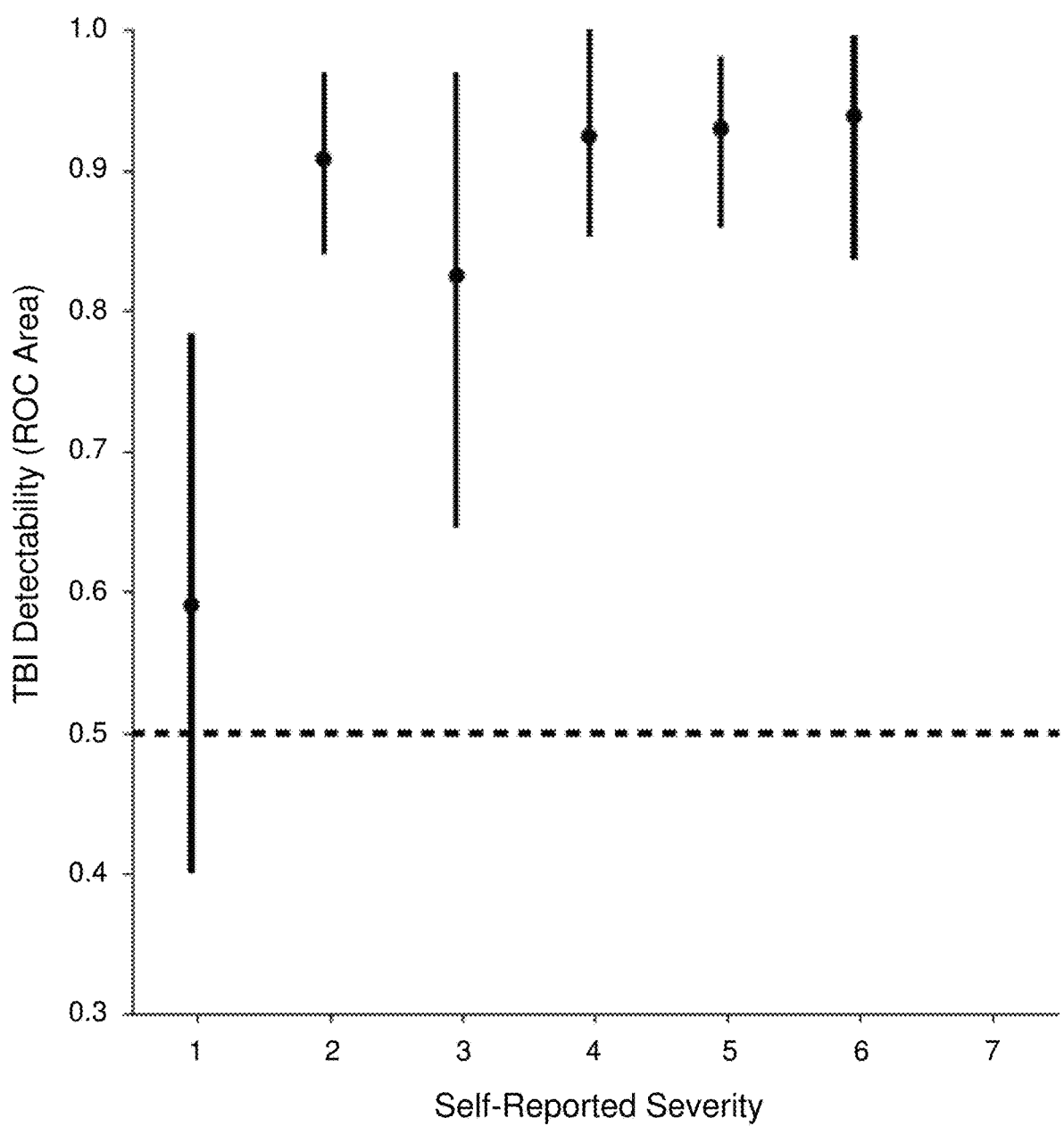
FIG. 4B is a graph illustrating the area under the Receiver Operating Characteristic (ROC) curves for each self-reported severity in the TBI population, according to some embodiments.

Second, the TBI impairment index was computed (Eq. (4)) for each TBI and control subject. FIG. 4A is a histogram 400 illustrating the TBI impairment indices (gray unfilled bars) and fitted normal distribution (solid gray curve, B) for the population of 34 TBI subjects along with the normal distribution of the control population of 41 subjects (solid black curve, A). Graph 410 of FIG. 4B plots the measured ROC curve area for each the self-reported severity in the TBI population. Filled black circles plot the average of 1,000 bootstrapped measurements for each of the severity levels. Error bars show the central 90% of the bootstrapped distribution. Inset text shows the number of TBI subjects at each self-reported severity level.

This index computes the scalar projection of a COBRA vector onto the TBI vector, quantifying how closely an individual's behavior matches typical TBI-related signs. Overall, the correlation between visual acuity and the TBI impairment index was not quite significant ($p=0.053$, $r=0.28$, Pearson's R), indicating that 92% of the variance in the TBI impairment index could not be attributed to static visual acuity problems.

To compute the overall detectability of TBI subjects using the two populations, computed the ROC curve area was computed for the two distributions (see FIG. 4A), which was 0.81. As control analyses, analogous ROC curve areas were computed for the subset of the TBI population (n=23) with visual acuity better than the $95^{th}$ percentile of the control population (their detectability was still 0.80) and for the subset of the TBI population (n=29) that fell within the age range (20 to 56 years) of the control population (their detectability was still 0.83). This shows that the detection by COBRA that a given TBI subject is not within the normal population is not an indirect consequence of the negligible mismatches in acuity or age between the overall TBI and control populations.

The entire TBI population was also subdivided according to self-reported severity, and the ROC curve area was computed for each severity level separately (See FIG. 4B). For observers reporting "little to no residual injury" (severity level of 1), their TBI detectability (0.59) was not significantly different than chance ($p>0.05$, bootstrap test), although it cannot be ruled out that the TBI detectability value was actually slightly higher than 0.5. For observers reporting more severe symptoms (severity level$\geq$2), TBI detectability was observed ranging from 0.85 to 0.95 (average 0.91). Furthermore, across the entire TBI population, significant correlation was observed between self-reported severity and TBI impairment index ($p<0.05$, $r=0.34$, Pearson's R).

Observations Gleaned from Experiment

As shown above, a non-invasive, 15-minute Comprehensive Oculometric Behavioral Response Assessment (COBRA) task generates ten performance metrics that quantify an individual's dynamic visuomotor processing capability. Also as shown above, COBRA provides a sensitive screening tool for detecting and characterizing impairments associated with TBI, even years after recovery. First, COBRA was used to quantify the characteristic constellation of TBI-related deficits in a population of 34 TBI subjects, expressed as a vector (i.e., the TBI vector). Presumably, non-TBI brain pathologies will show different characteristic vectors. Second, the TBI vector was used to quantify each subject's functional neurological impairment. Third, these TBI impairment indices were used to evaluate how well COBRA can detect TBI-related signs.

For the entire TBI population, COBRA could discriminate TBI subjects from controls with 81% probability. For the nine TBI subjects who reported "little-to-no" residual injury, TBI impairment indices were not statistically distinguishable from those of control subjects (only 58% probability of detection). For the 25 TBI subjects who reported substantial residual effects, COBRA discriminated them with 91% probability.

In general, using oculomotor measures to screen for neural pathology may hold potential shortcomings since not all brain structures mediate visuomotor behavior. Whereas a punctate hippocampal tumor is unlikely to cause any discernable impairment on familiar oculomotor tasks, the diffuse nature of TBI suggests that visuomotor tasks, which require a wide swath of cortical and cerebellar circuitry to estimate, predict, and track precise motion trajectories, are well-suited to detect such injuries. Even mild, yet diffuse, insults to neural circuitry may degrade the quality of the final output behavior. However, the oculomotor deficits observed among TBI subjects may also reflect factors that co-occur with TBI (e.g., stroke, medications, depression).

That said, differing visual, cognitive, and motor demands (e.g., executive function, response inhibition, attention, perception, expectation, prediction, memory, etc.) of various oculomotor paradigms (e.g., predictive tracking, gap/overlap saccades, antisaccades, memory-guided saccades, gaze conjugacy, etc.) likely engage specific brain networks to differing degrees. In particular, different degrees of injury affecting different networks may be necessary for specific oculomotor signs to be observed in any particular task (e.g., saccadic hypometria, poor saccadic inhibition, gaze disconjugacy, altered saccade dynamics, etc.). For example, head injury cases presenting with ocular motor nerve palsy are more severe than those without, suggesting that certain oculomotor signs (e.g., gaze disconjugacy) may occur following a threshold level of damage to a localized set of brainstem structures (i.e., $III^{rd}$, $IV^{th}$, or $VI^{th}$ cranial nerves and their associated nuclei), resulting in greater difficulty in detecting milder cases. To assay neural processing across a diverse set of brain areas, the COBRA vector of some embodiments uses a wider array of behaviors to capture the entire neural hierarchy of visuomotor processing: initial pursuit latency and acceleration driven by retinal slip, later direction tuning determined by extrastriate cortical processing associated with perception, catch-up saccades driven by anticipated retinal position error, and steady-state motion processing driven by perceived object motion.

In the experimental data (see FIG. 2), the magnitude of the deficits observed in the ten COBRA metrics differed. Although all ten tested metrics had negative mean values, four did not significantly differ from control metrics and two were only mildly impacted, whereas the remaining four were severely impacted. Because they all had similar variance, these four metrics had more statistical power to detect TBI than the remaining six. The value of having a large set of largely-independent COBRA measures is to increase the likelihood of detecting different types of pathologies. To go one step further, as the relationship between structural damage and functional impairment becomes better understood by pairing behavioral tests like COBRA with structural scans, anatomical explanations for the relatively-high detection power of certain oculometrics for certain pathologies (e.g., speed responsiveness for TBI) may develop, as well as the reason that others (e.g., gaze disconjugacy) are only observed in more severe cases. Of course, more statistically powerful, as-yet undescribed, behavioral metrics may be discovered, and are intended to be incorporated within some embodiments as far as vectorizing multiple metrics. A value of the impairment index of some embodiments is that a single scalar distills the ten metrics along the single direction most consistent with TBI and can easily be refined and extended as additional valuable and independent dimensions are discovered.

It should be emphasized that COBRA metrics are not only able to detect TBI-related impairment (see FIG. 4A), they also reflect TBI severity as documented by self-report. As a population, normally-distributed TBI impairment indices were observed that overlap the control population (see FIG. 4A), largely due to those TBI subjects with "little-to-no" residual injury (see FIG. 4B), and leaving those TBI subjects with meaningful residual injuries (severity level>2) discriminable at 91%. However, future studies of acute TBI patients with more clinically-rigorous measures of the severity of their neurological impairment (e.g., the x-axis of a future FIG. 4B) may be beneficial to further demonstrate the value of COBRA in clinical triage settings.

Based on work showing tight linkages between visual perception/cognition and oculomotor responses, the familiar association in neurology between oculomotor behavior and the function of certain cranial nerves and their associated brainstem nuclei can be expanded to include the ten COBRA metrics as neurological indicators of dynamic visuomotor processing at several functional stages: from retinal transduction, to cortical circuitry supporting motion perception and spatial attention, to the cortico-brainstem-cerebellar pathways supporting sensorimotor action. It can be concluded that characteristic datasets aggregated from standardized oculomotor test batteries (such as COBRA) may allow clinicians to detect, quantify, and characterize impairments from transient brain insults (e.g., due to trauma, drug toxicity, or alcohol) as well as permanent injuries, to detect the onset of degenerative, developmental, and psychiatric disorders and track their progression, and to evaluate the effectiveness of candidate therapeutic interventions, even in the absence of an individual baseline.

Figure 5:
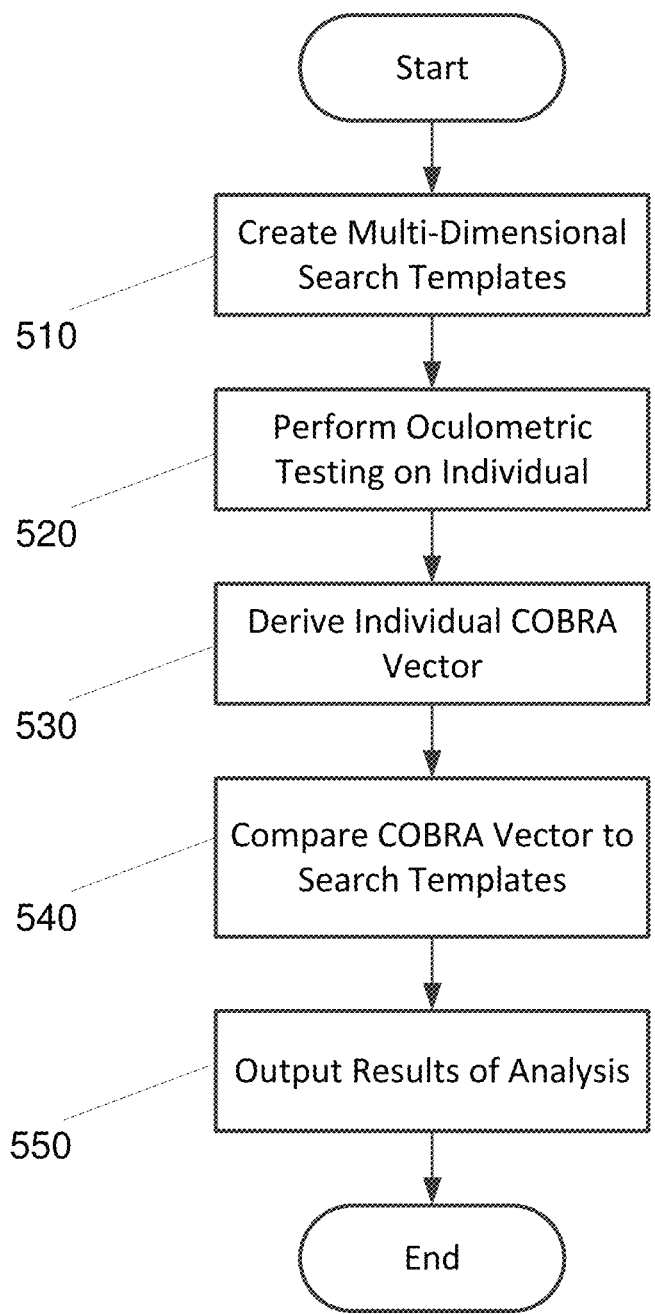
FIG. 5 is a flowchart illustrating a process for determining a type and severity of an individual's condition, according to some embodiments.

FIG. 5 is a flowchart 500 illustrating a process for determining a type and severity of an individual's condition, according to an embodiment of the present invention. The process begins with creating search templates for various conditions at 510. These search templates may be derived by testing a baseline population with no known conditions and testing groups of individuals with a single known condition (e.g., glaucoma, certain brain cancers, different types of TBI, various degrees of sleep deprivation, various degrees of drug or alcohol intoxication, etc.). The search templates may be vectors with a direction and amplitude. More specifically, to form the search templates, raw measurements from multi-dimensional results obtained during testing (e.g., COBRA data) are vectorized and averaged across the population of individuals with a given condition to yield a TBI vector.

Once search templates have been derived, an individual of interest is subjected to oculometric testing at 520. The oculometric testing provides a multi-dimensional representation of the individual's performance on various visual tests. The multi-dimensional results of the individual's oculometric testing are then used to derive a COBRA vector for the individual at 530 that can then be compared to the "impairment vectors" of the search templates.

The dot product may provide a measure of alignment with the template vector. As such, it is a measure of the angular difference, as well as the amplitude of the individual's COBRA vector itself. A large amplitude and close alignment would yield large impairment indices. However, large amplitude with a wide misalignment yields small impairment index. This provides evidence that such a large impairment is not due to TBI.

Once the COBRA vector has been determined, it is compared to one or more search templates at 540. In other words, the COBRA vector for the individual is analyzed against one or more of the search templates to produce mappings of the vector to the one or more search templates For instance, a computing system, may perform the comparison based on input from a neurologist or ophthalmologist, or the computing system may compare multiple (and perhaps many or all) search templates on its own to determine the most likely candidate or candidates for an individual's condition (or none at all if the individual does not correlate well with any condition's search template). The results of the analysis are then output for review at 550. For instance, by normalizing across the entire set of available search templates or by converting the impairment indices (in standard deviation units) into their corresponding p-score, the results may indicate that there is a 75% match with glaucoma, a 15% match with a concussion, a 5% match with diabetes, etc. A neurologist or ophthalmologist may then perform additional testing to confirm the condition, guided by the relative probabilities above.

Figure 8:
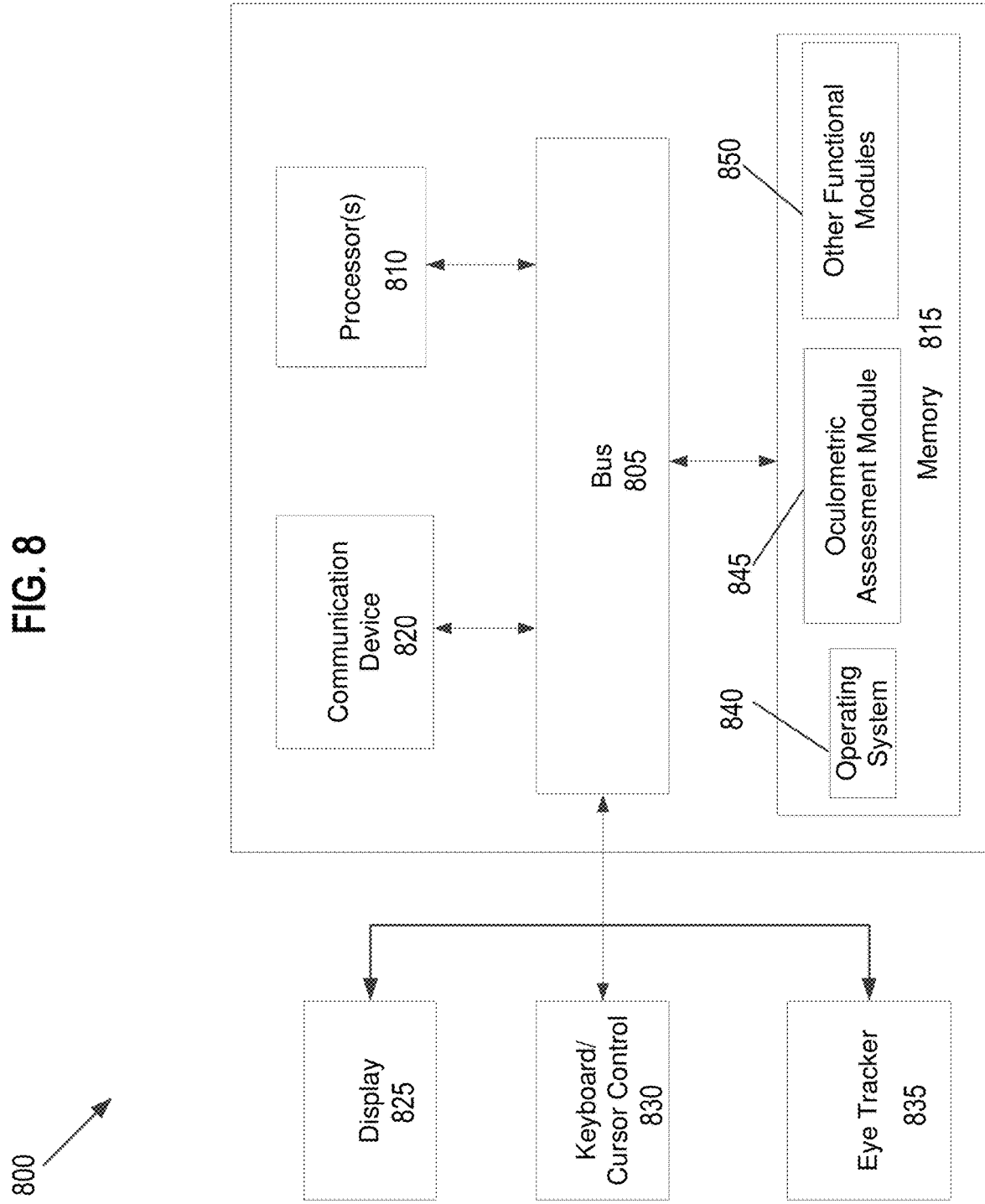
FIG. 8 is a block diagram of a computing system configured to perform oculometric assessment, according to an embodiment of the present invention.

FIG. 8 is a block diagram of a computing system 800 configured to perform oculometric assessment of sensorimotor impairment, according to an embodiment of the present invention. Computing system 800 includes a bus 805 or other communication mechanism for communicating information, and processor(s) 810 coupled to bus 805 for processing information. Processor(s) 810 may be any type of general or specific purpose processor, including a central processing unit (CPU) or application specific integrated circuit (ASIC). Processor(s) 810 may also have multiple processing cores, and at least some of the cores may be configured to perform specific functions. Multi-parallel processing may be used in some embodiments. Computing system 800 further includes a memory 815 for storing information and instructions to be executed by processor(s) 810. Memory 815 can be comprised of any combination of random access memory (RAM), read only memory (ROM), flash memory, cache, static storage such as a magnetic or optical disk, or any other types of non-transitory computer-readable media or combinations thereof. Additionally, computing system 800 includes a communication device 820, such as a transceiver and antenna, to wirelessly provide access to a communications network.

Non-transitory computer-readable media may be any available media that can be accessed by processor(s) 810 and may include both volatile and non-volatile media, removable and non-removable media, and communication media. Communication media may include computer-readable instructions, data structures, program modules or other data in a modulated data signal such as a carrier wave or other transport mechanism and includes any information delivery media.

Processor(s) 810 are further coupled via bus 805 to a display 825, such as a Liquid Crystal Display (LCD), for displaying information to a user. A keyboard and cursor control device 830, such as a computer mouse, are further coupled to bus 805 to enable a user to interface with computing system. However, in certain embodiments such as those for mobile computing implementations, a physical keyboard and mouse may not be present, and the user may interact with the device solely through display 825 (or virtual reality system) and/or a touchpad (not shown). Any type and combination of input devices may be used as a matter of design choice. An eye tracker 835 provides measurements of user eye position for the purposes of oculometric testing.

Memory 815 stores software modules that provide functionality when executed by processor(s) 810. The modules include an operating system 840 for computing system 800. The modules further include an oculometric assessment module 845 that is configured to analyze measurements of user eye movements, determine a disease vector for the user, and compare the disease vector to one or more search templates to determine a degree of matching to one or more conditions. Computing system 800 may include one or more additional functional modules 850 that include additional functionality.

One skilled in the art will appreciate that a "system" could be embodied as an embedded computing system, a personal computer, a server, a console, a personal digital assistant (PDA), a cell phone, a tablet computing device, a virtual or augmented reality headset, or any other suitable computing device, or combination of devices. Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology, including cloud computing systems.

It should be noted that some of the system features described in this specification have been presented as modules, in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, RAM, tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

The process steps performed in FIGS. 5 and 7 may be performed by a computer program, encoding instructions for the nonlinear adaptive processor to perform at least the process described in FIGS. 5 and 7, in accordance with embodiments of the present invention. The computer program may be embodied on a non-transitory computer-readable medium. The computer-readable medium may be, but is not limited to, a hard disk drive, a flash device, RAM, a tape, or any other such medium used to store data. The computer program may include encoded instructions for controlling the nonlinear adaptive processor to implement the process described in FIGS. 5 and 7, which may also be stored on the computer-readable medium.

The computer program can be implemented in hardware, software, or a hybrid implementation. The computer program can be composed of modules that are in operative communication with one another, and which are designed to pass information or instructions to display. The computer program can be configured to operate on a general purpose computer, or an ASIC.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A computer-implemented method for improved detection of clinical conditions for individuals, comprising:
    creating search templates for a plurality of clinical conditions, by a computing system, each search template comprising a vector in multi-dimensional space indicative of a respective clinical condition,
    wherein each search template is determined by:

$$\sum_{i=1}^{n}\left(\frac{COBRA_i}{n}\right)$$

where $COBRA_i$ is a Comprehensive Oculometric Behavioral Response Assessment (COBRA) vector for each individual with a given condition for the search template and n is a number of subjects with the condition;
    receiving, by the computing system, oculometric testing data collected from oculometric testing, the oculometric testing data including data collected from a randomized, radial tracking task performed on an individual and a plurality of oculometric measures collected from the individual, the plurality of oculometric measures collected by:
        receiving a first stream of camera and sensor data input of at least one or more of head, eye, and face data;
        coalescing the stream of data to determine one or more head positions captured in the first stream;
        receiving a second stream of high framerate optical camera input;
        extracting at least one or more of eye, pupil, retinal image data, and extracting at least one or more of motion of the said eye, pupil, or retinal image;
        fusing the first stream and the second stream to determine eye position within the head position for a plurality of common points in time;
        analyzing the fused data streams to produce the plurality of oculometric measures;
    creating a vector for the individual, by the computing system, based on the oculometric testing data;
    analyzing the vector for the individual, by the computing system, against one or more of the search templates; and
    producing an impairment index that is a projection of the vector for the individual onto the one or more search templates based on the analyzing, wherein the impairment index is a scalar measure of severity of the individual's clinical condition.

2. The computer-implemented method of claim 1, wherein the search templates are derived by testing a baseline population with no specific known abnormal conditions and testing groups of individuals with a single specific known abnormal condition for each respective search template.

3. The computer-implemented method of claim 2, wherein the creating of the search templates comprises vectorizing and averaging raw measurements from data obtained during testing across a population of individuals to yield the search template vector with a direction and an amplitude.

4. The computer-implemented method of claim 1, wherein the oculometric testing yields a multi-dimensional representation of the individual's performance on a plurality of visual tests.

5. The computer-implemented method of claim 1, further comprising:
    displaying ranked results, by the computing system, in an order from a most likely match to a least likely match of the vector of the individual to a plurality of the search templates.

6. The computer-implemented method of claim 1, wherein the creating of each search template further comprises:
    determining, by the computing system, a raw Comprehensive Oculometric Behavioral Response Assessment (COBRA) vector comprising a plurality of measurements for each individual having a condition associated with the search template;
    converting the plurality of measurements, by the computing system, into z-values relative to control data from a baseline population using:

$$\omega = \frac{RAW - CONTROL_{50th}}{\sigma}$$

where $\omega$ is a standard normalized metric, $$\sigma = \frac{(CONTROL_{75th} - CONTROL_{25th})}{2 \cdot \Phi^{-1}(0.75)},$$

and $\Phi^{-1}$ is the inverse of a normal cumulative distribution function.

7. The computer-implemented method of claim 1, wherein to produce the impairment index comprises determining the impairment index by taking a dot product of the vector for the individual and each search template and dividing the dot product by a scaling factor, and wherein the scaling factor is given by:

SCALING FACTOR=∥CHOL(COV(CONTROL))·TBI'∥ where CHOL is the Cholesky Decomposition, COV (CONTROL) is the covariance matrix of the population of control COBRA vectors, and TBI' is the transpose of the TBI vector.

8. A non-transitory computer-readable medium storing a computer program, the program configured to cause at least one processor to:
receive oculometric testing data collected from oculometric testing, the oculometric testing data including data collected from a randomized, radial tracking task performed on an individual and a plurality of oculometric measures collected from the individual, the plurality of oculometric measures collected by:
receiving a first stream of camera and sensor data input of at least one or more of head, eye, and face data;
coalescing the stream of data to determine one or more head positions captured in the first stream;
receiving a second stream of high framerate optical camera input;
extracting at least one or more of eye, pupil, retinal image data, and extracting at least one or more of motion of the said eye, pupil, or retinal image;
fusing the first stream and the second stream to determine eye position within the head position for a plurality of common points in time;
analyzing the fused data streams to produce the plurality of oculometric measures;
create a vector for the individual based on the oculometric testing data;
analyze the vector for the individual against a search template;
produce an impairment index that is a projection of the vector for the individual onto the search template based on the analyzing, the search template comprising a vector in multi-dimensional space indicative of a respective clinical condition, wherein the impairment index is a scalar measure of severity of the individual's clinical condition, wherein to produce the impairment index comprises determining the impairment index by taking a dot product of the vector for the individual and each search template and dividing the dot product by a scaling factor, and wherein the scaling factor is given by:

SCALING FACTOR=‖CHOL(COV(CONTROL))·TBI'‖ where CHOL is the Cholesky Decomposition, COV (CONTROL) is the covariance matrix of the population of control COBRA vectors, and TBI' is the transpose of the TBI vector.

9. The non-transitory computer-readable medium of claim 8, wherein the oculometric testing yields a multi-dimensional representation of the individual's performance on a plurality of visual tests.

10. The non-transitory computer-readable medium of claim 8, wherein the vector for the individual comprises a multi-dimensional Comprehensive Oculometric Behavioral Response Assessment (COBRA) vector having a direction and an amplitude.

11. The non-transitory computer-readable medium of claim 8, wherein the program is further configured to cause the at least one processor to:
create the search template by vectorizing and averaging raw measurements from data obtained during testing across a population of individuals to yield the search template vector with a direction and an amplitude, wherein the search template is derived by testing a baseline population with no specific known abnormal conditions and testing a group of individuals with a single specific known abnormal condition associated with the search template.

12. A computing system, comprising:
memory storing computer program code for performing oculometric assessment of sensorimotor impairment; and
at least one processor configured to execute the computer program code, the computing system configured to:
receive oculometric testing data collected from oculometric testing, the oculometric testing data including data collected from a randomized, radial tracking task performed on an individual and a plurality of oculometric measures collected from the individual, the plurality of oculometric measures collected by:
receiving a first stream of camera and sensor data input of at least one or more of head, eye, and face data;
coalescing the stream of data to determine one or more head positions captured in the first stream;
receiving a second stream of high framerate optical camera input;
extracting at least one or more of eye, pupil, retinal image data, and extracting at least one or more of motion of the said eye, pupil, or retinal image;
fusing the first stream and the second stream to determine eye position within the head position for a plurality of common points in time;
analyzing the fused data streams to produce the plurality of oculometric measures;
create a vector for the individual based on the oculometric testing data;
analyze the vector for the individual against a plurality of search templates, each search template comprising a vector in multi-dimensional space indicative of clinical a respective clinical condition, and
produce an impairment index based on the analysis that is a projection of the vector for the individual onto the search template based on the analyzing, wherein to produce the impairment index comprises determining the impairment index by taking a dot product of the vector for the individual and each search template and dividing the dot product by a scaling factor, and wherein the impairment index is a scalar measure of severity of the individual's clinical condition.

13. The computing system of claim 12, wherein the vector for the individual comprises a multi-dimensional Comprehensive Oculometric Behavioral Response Assessment (COBRA) vector having a direction and an amplitude.

14. The computing system of claim 12, wherein the computing system is further configured to:
create at least one search template by vectorizing and averaging raw measurements from data obtained during testing across a population of individuals to yield the search template vector with a direction and an amplitude, wherein the search template is derived by testing a baseline population with no specific known abnormal conditions and testing a group of individuals with a single specific known abnormal condition associated with the search template.

15. The computing system of claim 12, wherein the scaling factor is given by:

SCALING FACTOR=‖CHOL(COV(CONTROL))·TBI'‖ where CHOL is the Cholesky Decomposition, COV (CONTROL) is the covariance matrix of the population of control COBRA vectors, and TBI' is the transpose of the TBI vector.

* * * * *